United States Patent
Hashimoto et al.

(10) Patent No.: US 8,047,992 B2
(45) Date of Patent: Nov. 1, 2011

(54) BRIGHTNESS ADJUSTMENT METHOD AND SYSTEM FOR 3D ULTRASOUND

(75) Inventors: Shinichi Hashimoto, Otawara (JP); Tetsuya Kawagishi, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 977 days.

(21) Appl. No.: 11/738,820

(22) Filed: Apr. 23, 2007

(65) Prior Publication Data

US 2007/0265530 A1    Nov. 15, 2007

(30) Foreign Application Priority Data

Apr. 24, 2006 (JP) .................. 2006-119567
Mar. 16, 2007 (JP) .................. 2007-067960

(51) Int. Cl.
   *A61B 8/08* (2006.01)
(52) U.S. Cl. ...................... 600/443; 382/128
(58) Field of Classification Search .................. 600/437, 600/440–447, 458; 367/38, 65, 72; 73/602, 73/631; 382/128
See application file for complete search history.

(56) References Cited

U.S. PATENT DOCUMENTS

| | | | | |
|---|---|---|---|---|
| 4,180,790 A | * | 12/1979 | Thomas | 367/7 |
| 5,579,768 A | * | 12/1996 | Klesenski | 600/442 |
| 6,398,733 B1 | | 6/2002 | Simopoulos et al. | |
| 2005/0059892 A1 | | 3/2005 | Dubois et al. | |
| 2006/0241456 A1 | * | 10/2006 | Karasawa | 600/447 |
| 2007/0236492 A1 | * | 10/2007 | Ahn et al. | 345/418 |

FOREIGN PATENT DOCUMENTS

JP     2005-192900     7/2005
WO     WO 2004/107981 A1     12/2004

* cited by examiner

*Primary Examiner* — Parikha Mehta
(74) *Attorney, Agent, or Firm* — Oblon, Spivak, McClelland, Maier & Neustadt, L.L.P.

(57) ABSTRACT

An ultrasonic imaging apparatus comprises an ultrasonic probe, an image-processing part, a received signal intensity-adjusting part, and a display part. The ultrasonic probe three-dimensionally transmits/receives ultrasonic waves. The image-processing part generates a first ultrasonic image along a plane intersecting the scanning lines of ultrasonic waves, based on the signals obtained by transmitting/receiving of the ultrasonic waves. The signal intensity-adjusting part changes the intensity of the signals on the scanning lines passing through a brightness adjustment range for brightness adjustment set on the first ultrasonic image. The image-processing part generates a second ultrasonic image, based on the signal changed by the signal intensity-adjusting part. The display part displays the second ultrasonic image.

26 Claims, 13 Drawing Sheets

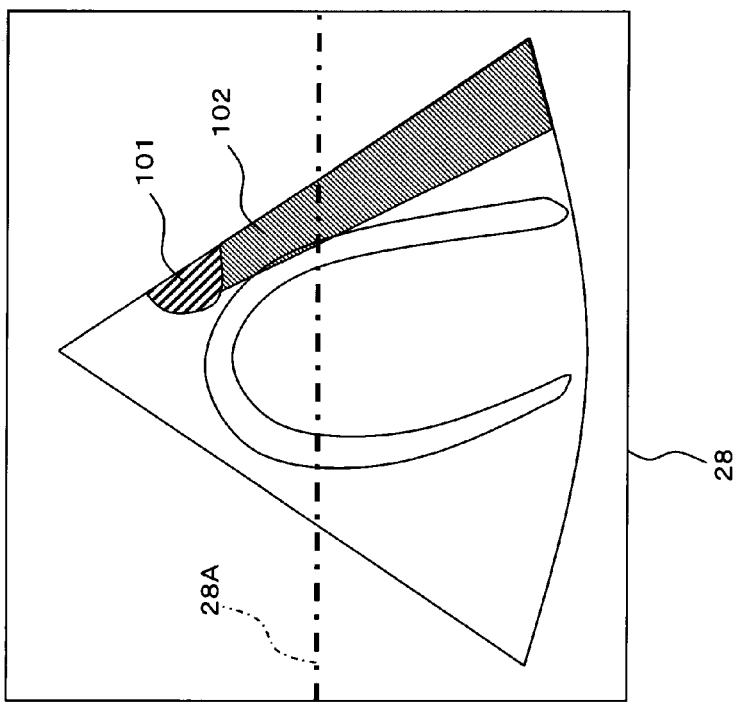
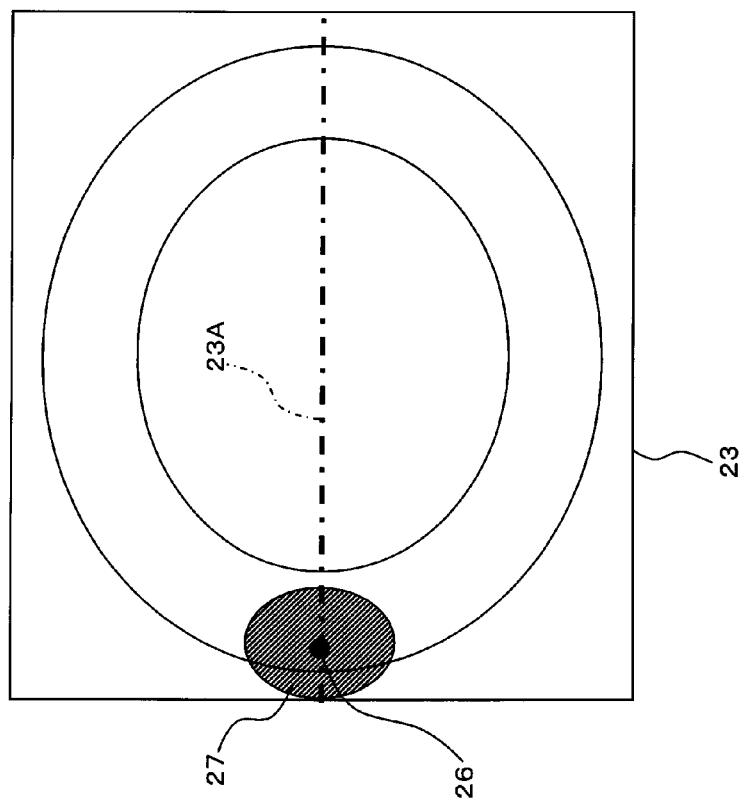
FIG. 5

FI.G 6

BRIGHTNESS ADJUSTMENT METHOD AND SYSTEM FOR 3D ULTRASOUND

BACKGROUND OF THE INVENTION

1. Field of the Invention

The present invention relates to an ultrasonic imaging apparatus for three-dimensional scanning and a method of obtaining ultrasonic images, and in particular, to a technology for adjusting the brightness of ultrasonic images.

2. Description of the Related Art

An ultrasonic imaging apparatus is capable of obtaining three-dimensional biological information and displaying a three-dimensional image by performing a 3D scan of a subject to be examined using ultrasonic waves.

On the other hand, even when an ultrasonic beam is transmitted under identical transmission conditions, the intensity of the received signal varies, depending on the orientation of the ultrasonic beam or the condition of the patient's body. For this reason, unevenness in illumination disadvantageously occurs for displaying the received signal as an ultrasonic image. Incidentally, the displayed ultrasonic image is displayed with contrasting density of brightness according to intensity of the received signal. An ultrasonic diagnosis apparatus for performing two-dimensional scans has an STC (Sensitivity Time Control) gain adjustment function for adjusting gain depthwise, or a function for adjusting gain laterally. When displaying a tomographic image that is a two-dimensional image, the brightness of the tomographic image may be adjusted by adjusting the gain depthwise or laterally (e.g., U.S. Pat. No. 6,398,733, which is incorporated herein by reference).

In addition, an ultrasonic imaging apparatus for automatically adjusting the gain for each scanning line, based on the distribution of brightness in pre-obtained ultrasonic images is known.

However, even if an attempt is made to automatically adjust the gain for each scanning line by automatically detecting the distribution of brightness in the ultrasonic image, the gain may not be appropriately adjusted. For example, when there is a highly reflective part in a short distance from the ultrasonic probe, the brightness of the short distance part becomes higher and the short distance part is brightly displayed while the brightness of the parts behind the short distance part (back regions) becomes low and the back regions are darkly displayed. When an ROI (region of interest) is placed in the back regions, it is very difficult to appropriately adjust the gain of the ROI, even if the gain is adjusted with the average value of the intensity (brightness) of the signal or with the intensity (brightness) of the signal in a predetermined depth.

For example, when observing a heart with a focus on the left ventricle by applying an ultrasonic probe to an apex, a peripheral part to be scanned becomes dark due to the ribs. For example, as the tomographic image 100 shown in FIG. 1, the ribs and surrounding cartilage are tissues through which ultrasonic waves cannot easily pass. Consequently, the ribs and cartilage become a highly reflective part (high brightness part) 101 for the ultrasonic waves, and the dark part 102 on the back may become dark.

When automatically adjusting gain, the average value of the intensity (brightness) of signals are calculated for each scanning line and the gain is adjusted for each scanning line so that the intensity (brightness) of the signal on each scanning line is uniform. However, as in the case of ribs, when a highly reflective part (high brightness part) is placed in a short distance from the ultrasonic probe, the average value of the intensity (brightness) of the signals on the scanning lines passing through that part becomes high. Therefore, it is difficult to automatically adjust it to an appropriate brightness.

When observing a tomographic image that is a two-dimensional image, an inspector can manually adjust the gain of an ROI by the STC gain adjustment or the gain adjustment laterally. However, in the case of an ultrasonic diagnosis apparatus for scanning three-dimensional space, the range for the gain adjustment is a three-dimensional space. Thus, it is difficult to specify an ROI, and consequently, the gain cannot be easily adjusted by only the STC gain adjustment and lateral gain adjustment.

SUMMARY OF THE INVENTION

The purpose of the present invention is to provide an ultrasonic imaging apparatus that is capable of easily adjusting the intensity of a signal when scanning a three-dimensional space, and a method of obtaining an ultrasonic image Embodiment 1 of the present invention is an ultrasonic imaging apparatus comprising an ultrasonic probe operable to three-dimensionally transmit/receive ultrasonic waves with an arrangement of ultrasonic transducers, an image-processing part operable to generate a first ultrasonic image along a plane intersecting the scanning lines of ultrasonic waves, based on signals obtained by said transmitting/receiving of ultrasonic waves, a display part operable to display said first ultrasonic image, and a signal intensity-adjusting part operable to change the intensity of the signals on the scanning lines passing through a brightness adjustment range for brightness adjustment set on said first ultrasonic image, wherein said image-processing part generates a second ultrasonic image based on signals changed by said signal intensity-adjusting part, and said display part displays said second ultrasonic image.

According to Embodiment 1, the range for adjustment of signal intensity is set, based on an ultrasonic image along a plane intersecting the scanning lines of ultrasonic waves, thus making it possible to easily set scanning lines whose signal intensities are to be adjusted in a three-dimensional space. Consequently, it becomes possible to easily adjust the intensity of the signals when scanning a three-dimensional space.

In addition, Embodiment 2 of the present invention is an ultrasonic imaging apparatus related to Embodiment 1, further comprising a designating part operable to designate a brightness adjustment range on the first ultrasonic image displayed on said display part, wherein said signal intensity-adjusting part changes the intensity of the signals on the scanning lines passing through said designated brightness adjustment range.

According to Embodiment 2, an ultrasonic image along a plane intersecting the scanning lines of ultrasonic waves is displayed on the display part and a range for adjustment signal intensity (an arbitrary range) is designated on the ultrasonic image, thereby making it possible to easily designate the scanning lines whose signal intensities are to be adjusted in a three-dimensional space. Consequently, it becomes possible to easily adjust the intensity of the signals when scanning a three-dimensional space.

In addition, the third embodiment of the present invention is a method of obtaining an ultrasonic image comprising: a) three-dimensionally transmitting/receiving ultrasonic waves by an ultrasonic probe on which ultrasonic transducers are arranged; b) generating a first ultrasonic image which is along a plane intersecting the scanning lines of ultrasonic waves, based on signals obtained by said transmitting/receiving of ultrasonic waves; c) changing the intensity of the signals on the scanning lines passing through a brightness adjustment range for brightness adjustment set on said first ultrasonic image; d) generating a second ultrasonic image based on the signals of which intensity is changed; and e) displaying said second ultrasonic image.

BRIEF DESCRIPTION OF THE DRAWINGS

FIG. 5 is a view of a monitor screen showing examples of the display of a tomographic image and a C plane image.

DETAILED DESCRIPTION OF THE EMBODIMENTS

Embodiment 1

(Configuration)

Figure 1:
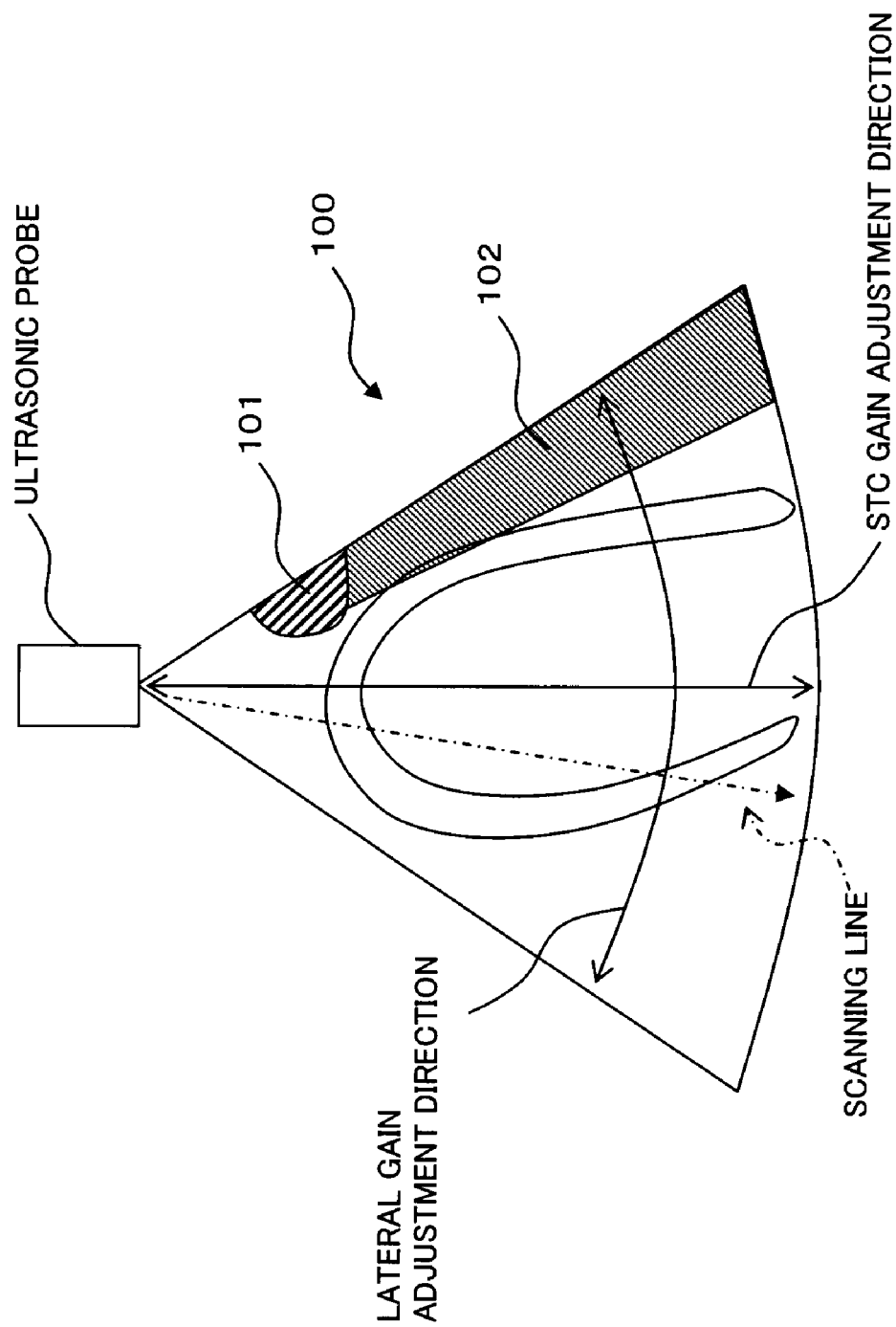
FIG. 1 is a view of a bright part and a dark part displayed in a tomographic image.
Figure 2:
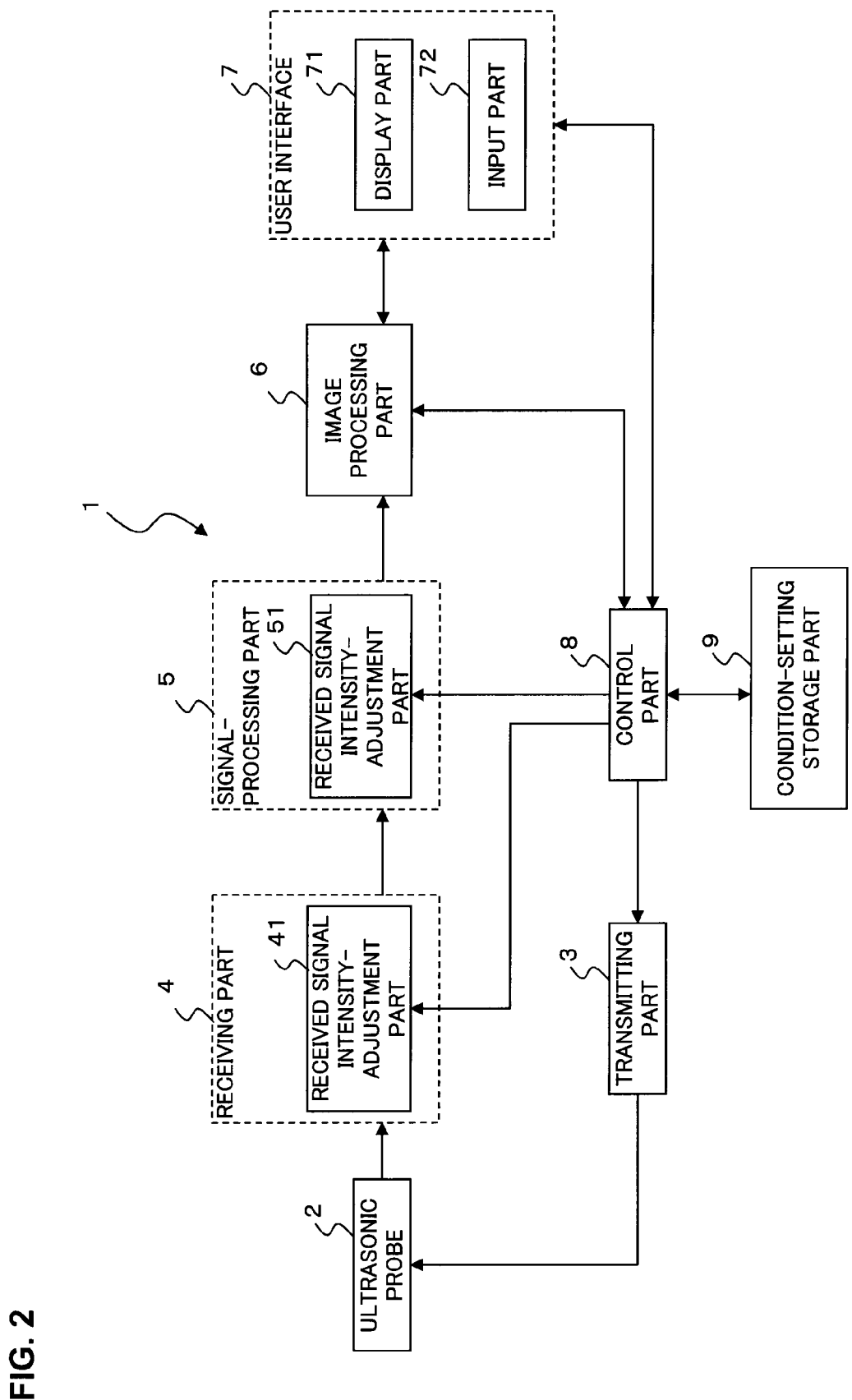
FIG. 2 is a block diagram showing the ultrasonic imaging apparatus related to Embodiment 1 of the present invention.

The configuration of an ultrasonic imaging apparatus related to Embodiment 1 of the present invention is described with reference to FIG. 2. FIG. 2 is a block diagram showing the ultrasonic imaging apparatus related to Embodiment 1 of the present invention.

The ultrasonic imaging apparatus 1 related to Embodiment 1 displays an ultrasonic image along a plane intersecting the scanning lines of ultrasonic waves on the display part 71. Then, an operator designates a range for gain adjustment on the ultrasonic image. As described, an ultrasonic image is displayed along a plane intersecting the scanning lines in order to easily designate scanning lines whose signal intensities are to be adjusted in a three-dimensional space. For example, the ultrasonic imaging apparatus 1 displays, on the display part 71, an ultrasonic image along a plane that is almost parallel to a plane on which ultrasonic transducers are arranged. Then, when the operator designates a range for gain adjustment on the ultrasonic image, the ultrasonic imaging apparatus 1 adjusts the gain of received signals included in the designated range. Thereby, the brightness of the ultrasonic image is adjusted. Hereinafter, each part of the ultrasonic imaging apparatus 1 is described.

The ultrasonic probe 2 may be a two-dimensional array probe or a one-dimensional array probe. On a two-dimensional array probe, ultrasonic transducers are two-dimensionally arranged. On a one-dimensional array probe, ultrasonic transducers are arranged in a predetermined direction (scanning direction). The two-dimensional array probe comprises ultrasonic transducers that are two-dimensionally arranged in order to three-dimensionally transmit ultrasonic waves and receive three-dimensional data of a region that radially spreads from the probe surface as an echo signal. In addition, the one-dimensional array probe can receive three-dimensional data as an echo signal by mechanically swinging the ultrasonic transducers in a direction perpendicular to the scanning direction. In the present embodiment, it may be a one-dimensional array probe, or a two-dimensional array probe.

Figure 3:
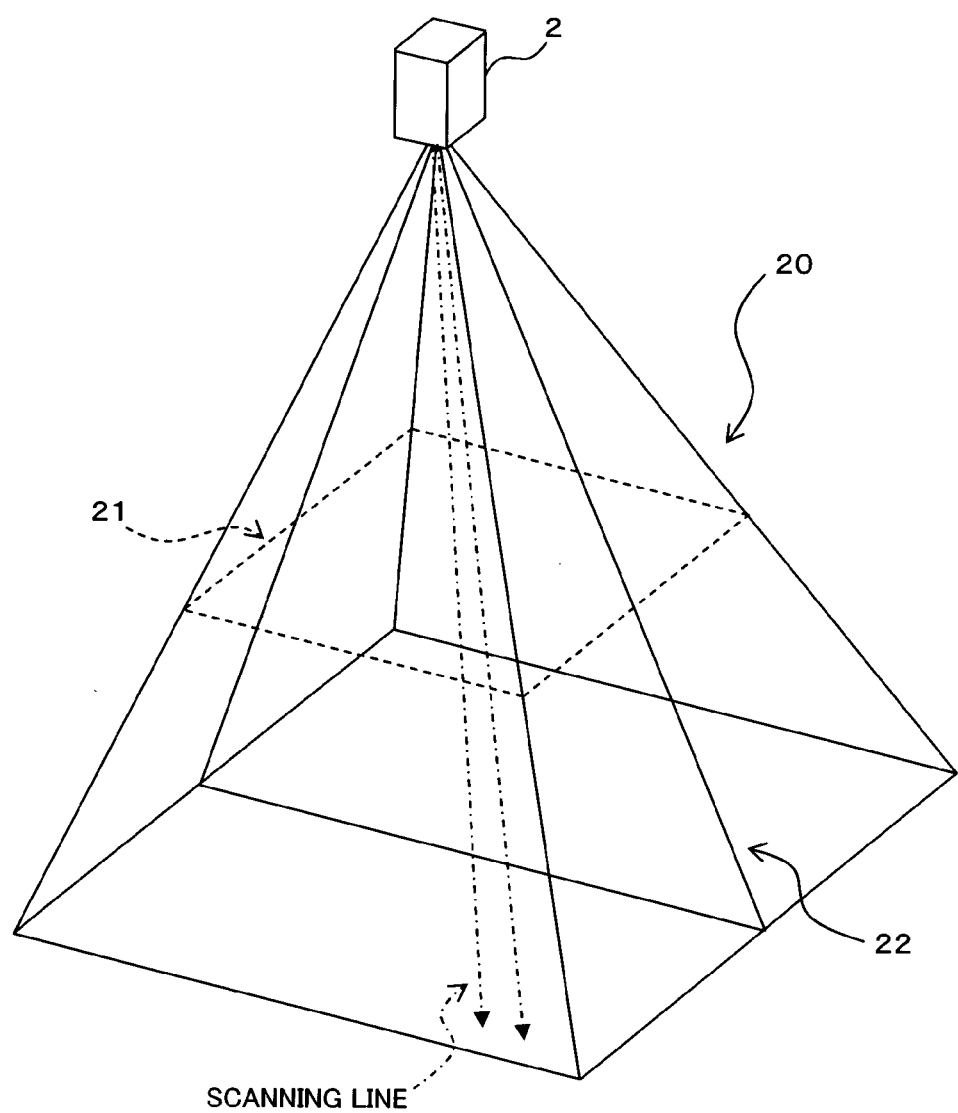
FIG. 3 is a schematic drawing showing a space to be scanned by ultrasonic waves.

Herein, the range to be scanned by ultrasonic waves is described with reference to FIG. 3. FIG. 3 is a schematic drawing showing a space to be scanned by ultrasonic waves. In the present embodiment, the ultrasonic probe is sector type as one example of the ultrasonic probe 2. FIG. 3 shows the range to be scanned by the ultrasonic probe. As shown in FIG. 3, the ultrasonic probe 2 of sector type can scan a square pyramid-shaped range from one original point using ultrasonic waves. In other words, the ultrasonic probe 2 can scan a scanning range 20 that is a three-dimensional space using ultrasonic waves.

A transmitting part 3 generates ultrasonic waves by supplying electrical signals to the ultrasonic probe 2. The transmitting part 3 is provided with a clock generation circuit, a transmission delay circuit, and a pulsar circuit, thereby supplying electrical signals to the ultrasonic probe 2 to generate ultrasonic waves. The clock generation circuit generates the clock signals to determine the transmission timing and/or the transmission frequency of the ultrasonic wave signal. The transmission delay circuit executes transmission focus by applying a delay when transmitting ultrasonic waves. The pulsar circuit housing pulsars as many as individual routings corresponding to each ultrasonic transducer generates a driving pulse at the delayed transmission timing to supply to each ultrasonic transducer of the ultrasonic probe 2.

A receiving part 4 is provided with a received signal intensity-adjusting part 41 (pre amplifier), an A/D conversion circuit, and a reception delay/adder circuit. The received signal intensity-adjusting part 41 (pre amplifier) adjusts the gain of the echo signals output from each ultrasonic transducer of the ultrasonic probe 2. Then, the received signal intensity-adjusting part 41 adjusts the gain for each signal on individual scanning lines. This gain adjustment by the received signal intensity-adjusting part 41 is performed for analog signals before they are converted into digital signals, so this gain adjustment is referred to as analog gain adjustment for the sake of convenience.

In addition, the A/D conversion circuit provides A/D conversion of echo signals amplified by the received signal intensity-adjusting part 41. The reception delay/adder circuit provides and/or adds a delay time required to determine the receiving directivity to the echo signals provided with the A/D conversion by the A/D conversion circuit. With this addition, the reflected component in the direction of the receiving directivity is emphasized.

A signal-processing part 5 mainly comprises a B-mode processing part. Herein, the B-mode processing part converts the amplitude information of the echo to an image and generates B-mode ultrasonic raster data from the echo signals. Specifically, the B-mode processing part executes band pass filter processing on the signals output from the receiving part 4, and then detects the envelope of the output signals, and applies compression processing to the detected data by means of logarithmic conversion to generate data. Incidentally, the signal-processing part 5 may be provided with a doppler processing part and a CFM (Color Flow Mapping) processing part instead of the B-mode processing part.

In addition, the signal-processing part 5 is provided with a received signal intensity-adjusting part 51. This received signal intensity-adjusting part 51 performs gain adjustment for the signals output from the receiving part 4 and converted from analog signals into digital signals. This received signal intensity-adjusting part 51 adjusts the gain for each signal on individual scanning lines. This gain adjustment by the received signal intensity-adjusting part 51 is performed for the signals after they are converted from analog signals into digital signals, so this gain adjustment is referred to as digital gain adjustment for the sake of convenience.

The ultrasonic imaging apparatus 1 related to Embodiment 1 performs analog gain adjustment by the received signal intensity-adjusting part 41 of the receiving part 4 or the digital gain adjustment by the received signal intensity-adjusting part 51 of the signal-processing part 5. In addition, after the received signal intensity-adjusting part 41 of the receiving part 4 performs the analog gain adjustment, the received signal intensity-adjusting part 51 of the signal-processing part 5 may further perform the digital gain adjustment. In other words, the intensity of received signals may be adjusted by executing both the analog gain adjustment and the digital gain adjustment.

The image-processing part 6 applies various image processing to image data obtained by scanning with the ultrasonic probe 2. For example, when a volume scan (3D scan) is performed using the ultrasonic probe 2, the image-processing part 6 generates three-dimensional image data by applying volume rendering to volume data.

Instead of volume rendering, the image-processing part 6 can also apply image processing such as MPR (Multi Plane Reconstruction) processing. For example, the image-processing part 6 applies the MPR processing to the volume data so as to generate an image (hereinafter, referred to as "MPR image") into which the volume data is cut with an arbitrary plane (cutting plane). The operator can optionally designate this cutting plane.

For example, the image-processing part 6 generates image data (hereinafter, referred to as "C plane image data") along a plane parallel to a plane (hereinafter, referred to as "C plane") on which ultrasonic transducers are arranged, or generates image data (hereinafter, referred to as "tomographic image data") along a plane (hereinafter, referred to as "tomographic plane") perpendicular to the C plane. Herein, the C plane and the tomographic plane are described with reference to FIG. 3.

As shown in FIG. 3, the C plane 21 and the tomographic plane 22 are perpendicular to each other. In addition, the C plane 21 is perpendicular to the scanning lines of ultrasonic waves shown in FIG. 3. On the other hand, the tomographic plane 22 is a plane along the scanning lines and includes the scanning lines. The operator can change the positions of the C plane 21 and the tomographic plane 22 by using an input part 72. For example, the position of the C plane 21 can be specified by designating a distance from the ultrasonic probe 2.

For example, when the operator designates the C plane 21, the image-processing part 6 generates image data along the C plane 21 (C plane image data) based on volume data. In addition, when the operator designates the tomographic plane 22, the image-processing part 6 generates image data along the tomographic plane 22 (tomographic image data) based on volume data. The C plane image data or the tomographic image data generated in this way is output by the image-processing part 6 onto a display part 71 of a user interface 7.

Upon receipt of image data, such as three-dimensional image data, tomographic image data, or C plane image data, from the image-processing part 6, the display part 71 displays an image based on the image data. For example, an ultrasonic image such as a three-dimensional image, a tomographic image, or a C plane image is displayed on the monitor screen of the display part 71.

The C plane image and the tomographic image are described by way of examples in Embodiment 1. Incidentally, when a plane other than the C plane or the tomographic plane is designated by the operator, the image-processing part 6 generates image data along the designated plane and instructs the display part 71 to display an image based on the image data.

The input part 72 is an input device for various settings related to transmitting/receiving conditions of ultrasonic waves. The operator can use the input part 72 to designate a range for gain adjustment, to input gain, or to designate a cutting plane for generating a MPR image.

Herein, gain setting and the designation of a range for gain adjustment are described. In Embodiment 1, the image-processing part 6 generates image data of a plane intersecting the scanning lines of ultrasonic waves and instructs the display part 71 to display an image based on the image data. Then, the operator uses the input part 72 to designate a range for gain adjustment on the image. As described, the display part 71 displays an image of a plane intersecting the scanning lines so that the operator can easily capture the position of scanning lines for gain adjustment in a three-dimensional space. For example, the C plane intersects the scanning lines of ultrasonic waves. Consequently, the C plane image is displayed on the display part 71 and the region for gain adjustment is designated on the C plane image so as to easily capture and designate a range for gain adjustment in a three-dimensional space.

Figure 4A:
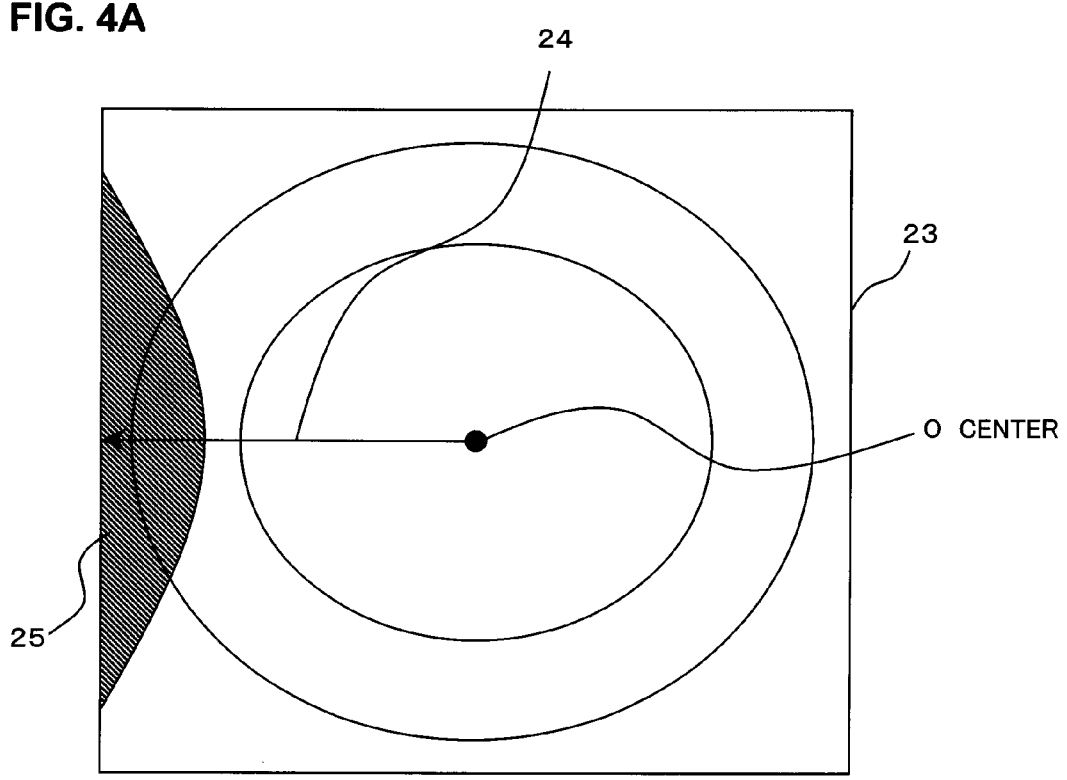
FIG. 4A is a view of a monitor screen showing an example of the display of a C plane image.
Figure 4B:
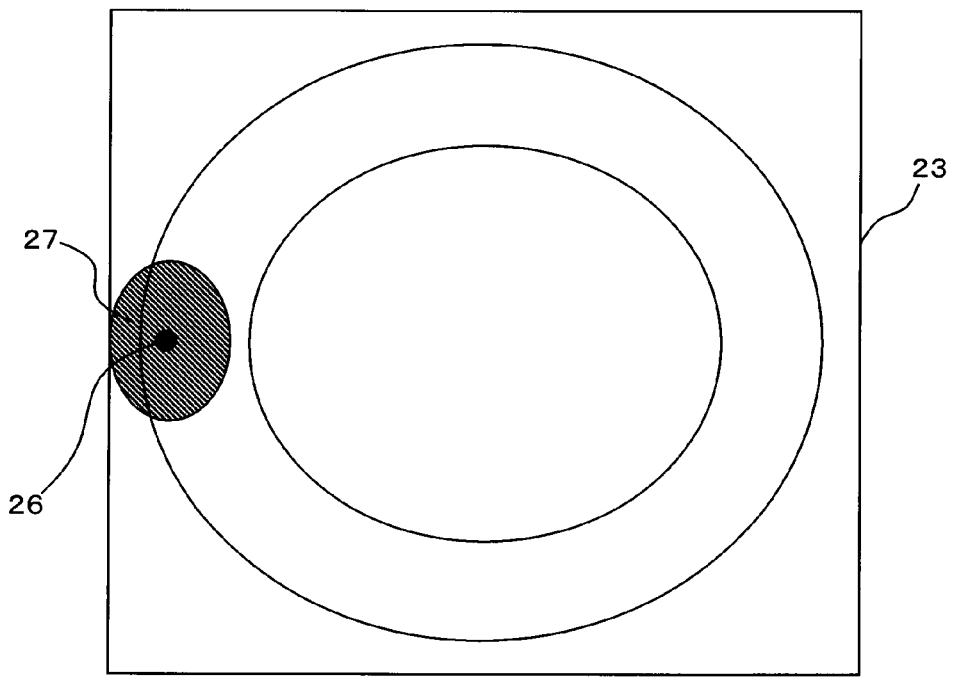
FIG. 4B is a view of a monitor screen showing an example of the display of a C plane image.
Figure 6:
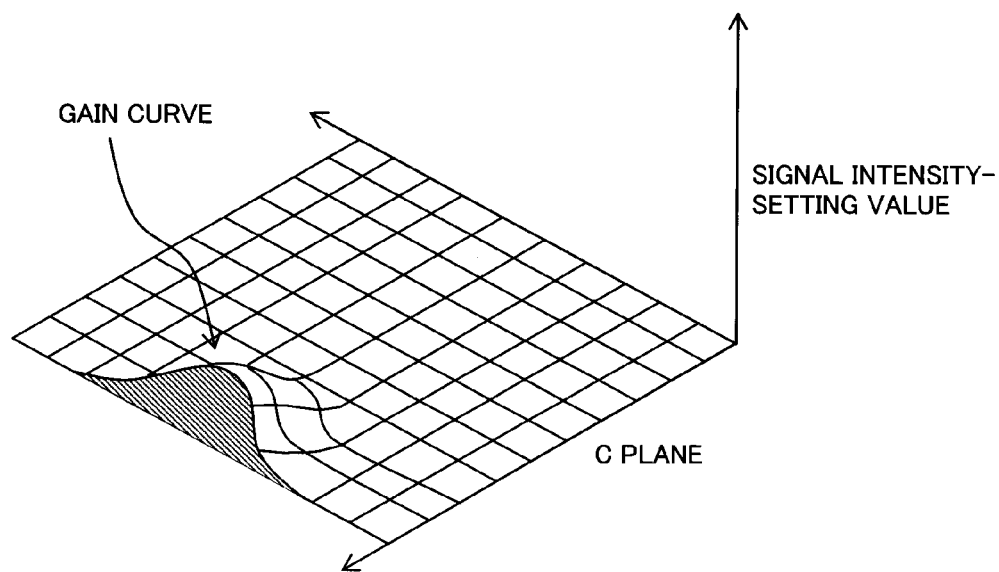
FIG. 6 shows one example of a gain curve.

The designation of a range for gain adjustment and one example of gain settings are described with reference to FIG. 4A, FIG. 4B, FIG. 5, and FIG. 6. FIG. 4A and FIG. 4B are views of a monitor screen showing an example of the display of a C plane image. FIG. 5 is a view of a monitor screen showing examples of the display of a tomographic image and a C plane image. FIG. 6 shows one example of a gain curve.

When volume data is obtained by performing a volume scan (3D scan) using the ultrasonic probe 2, the image-processing part 6 generates image data along the C plane (C plane image data) designated by the operator based to the volume data. Incidentally, the operator can use the input part 72 to designate a distance (depth) from the ultrasonic probe 2 to designate the position of the C plane. The C plane image data generated by the image-processing part 6 is displayed on the monitor screen of the display part 71.

As shown in FIG. 4A and FIG. 4B, the C plane image 23 of a section for diagnosis (e.g., heart) is displayed on the display part 71. The operator uses the input part 72 to designate a range for gain adjustment on the C plane image 23. For example, as shown in FIG. 4A, when the operator uses the input part 72 to designate a direction 24 from the center O of the C plane image 23 toward the peripheral part, a preset range from the peripheral part of the designated direction inward is set as a range 25 for gain adjustment. The brightness of the peripheral part of the C plane image 23 is low, so the designated range 25 corresponds to the dark part. As already mentioned, only by designating a direction from the center toward the peripheral part, a range corresponding to the dark part may be easily set as a range for gain adjustment. Incidentally, the operator can optionally change the width of the range 25.

Then, coordinate information of the range 25 designated on the C plane is output from the user interface 7 to the image-processing part 6. The image-processing part 6 specifies scanning lines passing through the coordinates from the coordinate information of the range 25, and outputs the information indicating the positions of the scanning lines (coordinate information) to a control part 8.

In addition, as shown in FIG. 4B, when the operator uses the input part 72 to designate an arbitrary point 26 on the C plane image 23, a preset size of range centered on the point 26 is set as a range 27 for gain adjustment. Then, coordinate information of the range 27 designated on the C plane is output from the user interface 7 to the image-processing part 6. The image-processing part 6 specifies scanning lines passing through the coordinate from the coordinate information of the designated range 27, and outputs the information indicating the positions of the scanning lines (coordinate information) to a control part 8. As described, only by designating a arbitrary point, a range for gain adjustment may be easily set. Incidentally, the operator can optionally change the size and shape of the range 27.

Upon receipt of the coordinate information (information indicating the positions of the scanning lines) of the range for gain adjustment from the image-processing part 6, the control part 8 determines the gain for signals on each scanning line passing through the range. For example, a gain curve that associates coordinates of the C plane with signal intensity-setting values is pre-stored on a condition-setting storage part 9. In accordance with the gain curve, the control part 8 determines the gain for signals on each scanning line passing through the range for gain adjustment. In addition, the operator may also use the input part 72 to designate a gain curve. For example, the operator inputs a pattern of the gain curve associating coordinates on the C plane with signal intensity-setting values shown in FIG. 6, or changes the preset gain curve, thereby determining the gain of a range for gain adjustment.

In addition, the control part 8 determines a gain value so that the signal intensities are consecutive inside and outside of the range for gain adjustment. For example, the control part 8 sets the gain to the highest near the center of the range for gain adjustment, and sets the gain to gradually lower toward the peripheral of the range for gain adjustment. As described, it is possible to gradually change the signal intensity depending on the position within the range for gain adjustment by gradually changing the gain depending on the position. Consequently, the intensity of signals can be consecutively changed at the boundary between inside and outside of the range for gain adjustment, so an image without irregularity in the brightness values can be obtained.

As described above, when the position of scanning lines and the gain is determined, the control part 8 outputs the information indicating the positions of the scanning lines (coordinate information) and the gain to the received signal intensity-adjusting part 41 of the receiving part 4.

Upon receipt of the information indicating the positions of the scanning lines and the gain from the control part 8, the received signal intensity-adjusting part 41 of the receiving part 4 changes the intensity of the signals on the scanning lines among signals output from the ultrasonic probe 2 in accordance with the gain. The received signals which intensity is changed as above are output to the image-processing part 6 through the signal-processing part 5.

The image-processing part 6 generates three-dimensional image data by performing volume rendering, or generates image data of an arbitrary cross section by performing the MPR processing. An image such as a three-dimensional image or a tomographic image whose signal intensity is changed is displayed on the display part 71. Consequently, an image whose brightness is changed in the range designated by the operator is displayed on the display part 71. For example, when a range corresponding to a dark part is designated as a range for gain adjustment, an image whose brightness is changed in the dark part is displayed on the display part 71.

In addition, when designating a range for gain adjustment, not only the C plane image, but also the tomographic image along the plane perpendicular to the C plane may be displayed on the display part 71. The image-processing part 6 generates image data along the C plane (C plane image data) by applying the MPR processing to volume data, further generates image data along a plane perpendicular to the C plane (tomographic plane) (tomographic image data), and then outputs the C plane image data and the tomographic image data to the display part 71. Consequently, as shown in FIG. 5, a C plane image 23 and a tomographic image 28 perpendicular to the C plane image 23 are displayed on the display part 71. Then, the operator uses the input part 72 to designate a range 27 for gain adjustment on the C plane image 23. As described, by displaying the C plane image 23 for designating a range for gain adjustment and the image of the plane perpendicular to the C plane (the tomographic image 28) on the display part 71 at the same time, the three-dimensional space is more easily captured; thus, making it easier to designate a range for gain adjustment.

In addition, the image-processing part 6 may instruct to display a line 28A indicating the position of the C plane on the tomographic image 28, so that the operator can visually recognize the distance (depth) from the ultrasonic probe 2 to the C plane. At this time, the image-processing part 6 may display a line 23A that indicates the position of the tomographic plane on the C plane image 23.

Furthermore, in Embodiment 1, the range for gain adjustment is designated on the C plane image 23, however, the range for gain adjustment may be designated on an image other than the C plane image 23. This is because that, even an image other than the C plane facilitates to designate a range (scanning lines) for gain adjustment, as long as it is an image along a plane intersecting the scanning lines of ultrasonic waves.

In this case, when the operator uses the input part 72 to designate an arbitrary cut plane, the image-processing part 6 generates image data along the designated cut plane based on volume data. An image based on the image data is displayed on the display part 71, and then the operator uses the input part 72 to designate a range for gain adjustment on the image. As described, even when displaying an image other than the C plane image, designation of the range (scanning lines) for gain adjustment can be facilitated.

In addition, the control part 8 is connected to each part of the ultrasonic imaging apparatus 1 to control operations of each part. For example, the control part 8 administrates control over the transmitting processing by the transmitting part 3, control over the receiving processing by the receiving part 4, control over the signal processing by the signal-processing part 5, control over the image processing by the image-processing part 6, and control over the display processing and input processing by the user interface 7.

In addition, the received signal intensity-adjusting part 41, the received signal intensity-adjusting part 51, the image-processing part 6, and the control part 8 may be implemented by hardware, or may be implemented by software. For example, the received signal intensity-adjusting part 41, the received signal intensity-adjusting part 51, the image-processing part 6, and the control part 8 are implemented by a CPU (Central Processing Unit), respectively. Then, a first received signal intensity adjusting program for executing functions of the received signal intensity-adjusting part 41, a second received signal intensity adjusting program for executing functions of the received signal intensity-adjusting part 51, an image processing program for executing functions of the image-processing part 6, and a program for executing functions of the control part 8 are pre-stored on a not shown storage part. Then, the CPU executes functions of the received signal intensity-adjusting part 41 by executing the first received signal intensity adjusting program stored on the not shown storage part. In addition, the CPU executes functions of the received signal intensity-adjusting part 51 by executing the second received signal intensity adjusting program. In addition, the CPU executes functions of the image-processing part 6 by executing the image processing program. In addition, the CPU executes functions of the control part 8 by executing a program executing functions of the control part 8.

Operation

Figure 7:
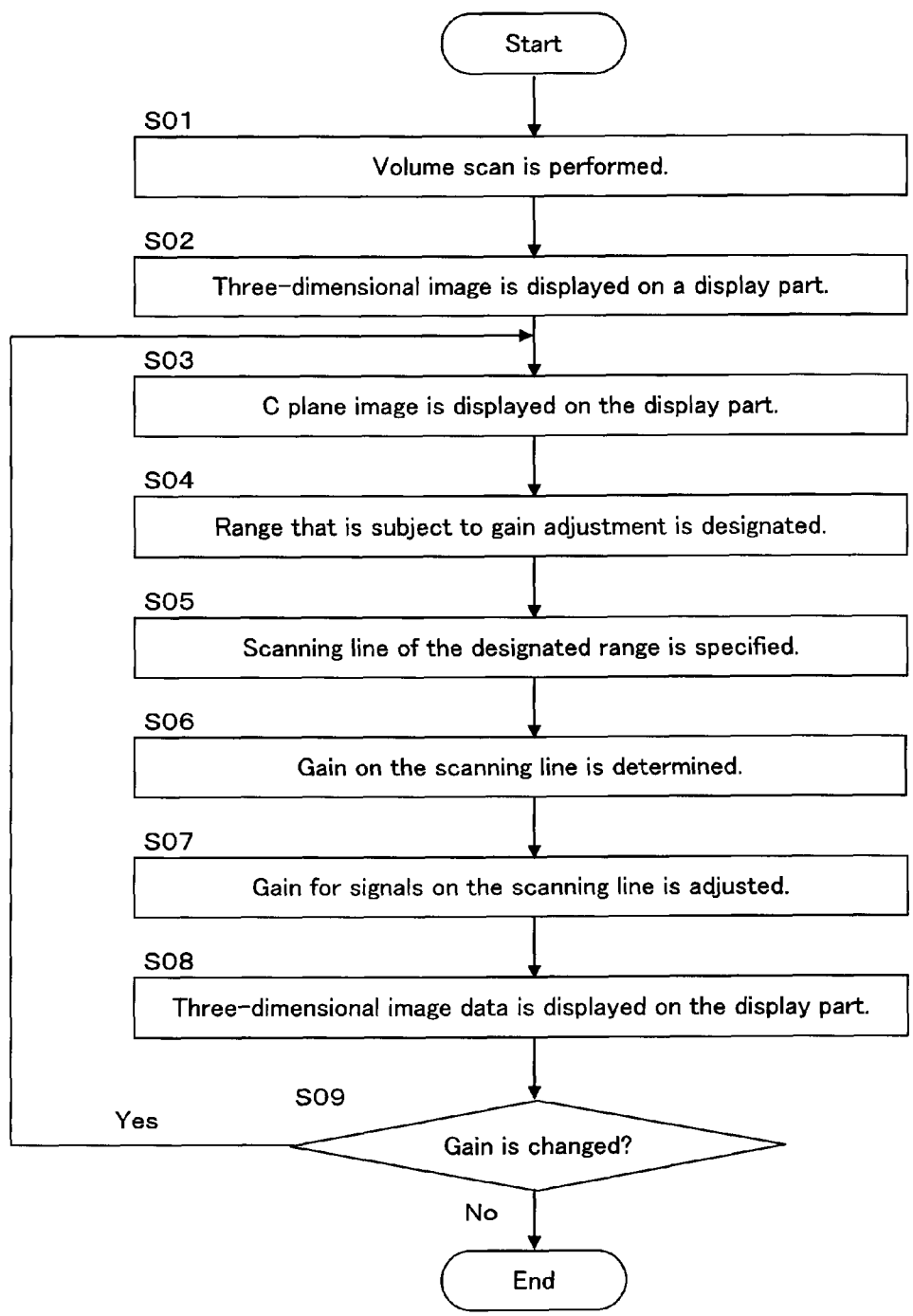
FIG. 7 is a flow chart sequentially showing operations of the ultrasonic imaging apparatus related to Embodiment 1 of the present invention.

Next, the operation of the ultrasonic imaging apparatus 1 related to Embodiment 1 of the present invention is described with reference to FIG. 7. FIG. 7 is a flow chart sequentially showing operations of the ultrasonic imaging apparatus related to Embodiment 1 of the present invention.

Step S01

First, by applying the ultrasonic probe 2 to the body surface of a subject to be examined, a volume scan (3D scan) is performed using the ultrasonic probe 2.

Step S02

The image-processing part 6 generates a three-dimensional image data by applying volume rendering to the volume data obtained by the scan using the ultrasonic probe 2. A three-dimensional image based on this three-dimensional image data is displayed on the display part 71.

Step S03

Then, when the operator gives an instruction of gain adjustment via the input part 72, the image-processing part 6 generates image data of an arbitrary cross section by applying the MPR processing to volume data. For example, when the operator designates an arbitrary C plane (depth) via the input part 72, the image-processing part 6 generates image data along the C plane (C plane image data). A C plane image based on this C plane image data is displayed on the display part 71.

Step S04

In the state where the C plane image is displayed on the display part 71, the operator designates an arbitrary range on the C plane image via the input part 72. This designated range is set as a range for gain adjustment. For example, as shown in FIG. 4A, when the operator designates a direction 24 on a C plane image 23 via the input part 72, a peripheral part of the C plane image 23 is set as a range 25 for gain adjustment. Then, coordinate information of the designated range 25 is output from the user interface 7 to the image-processing part 6. In addition, as shown in FIG. 4B, when the operator designates a point 26 on the C plane image 23 via the input part 72, a range centered on the point 26 is set as a range 27 for gain adjustment. Coordinate information of the designated range 27 is output from the user interface 7 to the image-processing part 6.

Step S05

Upon receipt of the coordinate information of the range for gain adjustment from the input part 72, the image-processing part 6 specifies scanning lines passing through the range and outputs the information indicating the positions of the scanning lines to the control part 8.

Step S06

Upon receipt of the coordinate information of the range for gain adjustment from the image-processing part 6, the control part 8 determines the gain for signals on each scanning line passing through the range. For example, when the operator designates a gain curve via the input part 72, the control part 8 determines the gain for signals on each scanning line passing through the range for gain adjustment in accordance with the gain curve. In addition, by pre-storing a gain curve on the condition-setting storage part 9, the control part 8 determines the gain for signals on each scanning line passing through the range for gain adjustment in accordance with the gain curve. Incidentally, the control part 8 determines the gain so that the signal intensities are consecutive inside and outside of the range for gain adjustment. For example, the control part 8 sets the gain to the highest near the center of the range for gain adjustment, and sets the gain to gradually lower from the center toward the peripheral. When the gain is determined as above, the control part 8 outputs information indicating the positions of the scanning lines and the gain to the received signal intensity-adjusting part 41 of the receiving part 4.

Step S07

Upon receipt of the information indicating the positions of the scanning lines and the gain from the control part 8, the received signal intensity-adjusting part 41 of the receiving part 4 adjusts the intensity of signals output from the ultrasonic probe 2, the signals being on the designated each scanning line in accordance with the gain. Then, the adjusted signals are output to the image-processing part 6 via the signal-processing part 5.

Step S08

The image-processing part 6 generates image data such as three-dimensional image data by applying image processing such as volume rendering to the gain-adjusted volume data. An image based on this image data is displayed on the display part 71. This image is a gain-adjusted image, accordingly an image whose brightness is adjusted. For example, if the gain of a dark part is adjusted, the brightness of the dark part is high, resulting in that an image in which the brightness is wholly uniform is obtained.

Step S09

The operator observes this gain-adjusted image to determine whether change in the set gain is necessary or not (Step S09). For example, it is determined that there is no need to change the gain when the brightness of the range to be observed (ROI) is appropriate. On the other hand, it is determined that there is a need to change the gain when the brightness is too low to observe. Then, when it is determined that there is a need to change the gain, the operator gives an instruction of gain adjustment via the input part 72 (Step S09, Yes). Consequently, processing from step S03 to step S08 are repeated. At this time, the operator gives an instruction of brightness adjustment by changing a range to be gain-adjusted or by changing a gain curve. On the other hand, when the operator determines that there is no need to change the gain, the received signal intensity-adjusting part 41 performs gain adjustment to signals to be obtained afterward in accordance with the gain and the range of gain adjustment set by from step S03 to step S08.

As described above, it becomes possible to easily designate scanning lines for gain adjustment in a three-dimensional space by displaying a C plane image intersecting the scanning lines of ultrasonic waves and by designating the range for gain adjustment on the C plane image.

In addition, as shown in FIG. 5, by displaying an image (tomographic image 28) along a plane perpendicular to the C plane (tomographic plane) on the display part 71 at the time of displaying the C plane image 23, the range for gain adjustment may be designated on the C plane image 23 while observing the tomographic image 28. As described, by displaying the tomographic image 28 at the time of displaying the C plane image 23, capturing a position in a three-dimensional space is facilitated.

Furthermore, in Embodiment 1, gain adjustment is performed for analog signals before conversion into digital signals, however, gain adjustment may be performed after converting analog signals into digital signals. In this case, at step S06, the control part 8 outputs information indicating the positions of scanning lines and the gain to the received signal intensity-adjusting part 51 of the signal-processing part 5. Upon receipt of the information indicating the positions of the scanning lines and the gain from the control part 8, the received signal intensity-adjusting part 51 of the signal-processing part 5 adjusts the intensity of signals after conversion into digital signals, the signals being on the designated each scanning line, in accordance with the gain. Then, the adjusted signals are output to the image-processing part 6. Incidentally, the designation of a range to be gain-adjusted is as described above.

In addition, gain adjustment is performed for an analog signal before conversion into a digital signal, and furthermore, gain adjustment may also be performed for the signal after conversion into signal.

Embodiment 2

Figure 8:
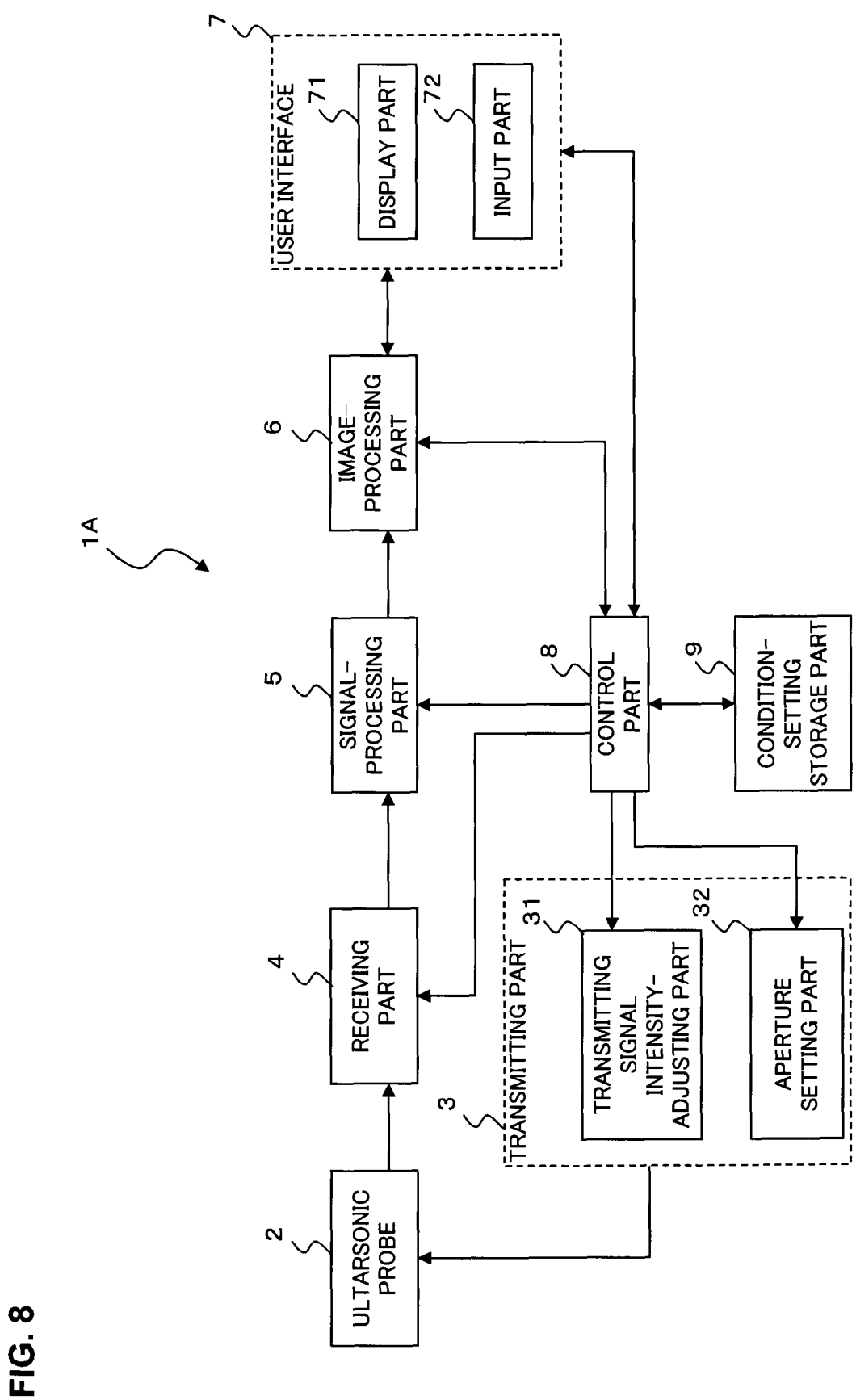
FIG. 8 is a block diagram showing the ultrasonic imaging apparatus related to Embodiment 2 of the present invention.

The configuration of the ultrasonic imaging apparatus related to Embodiment 2 of the present invention is described with reference to FIG. 8. FIG. 8 is a block diagram showing the ultrasonic imaging apparatus related to Embodiment 2 of the present invention.

The ultrasonic imaging apparatus 1A related to Embodiment 2, as is the case with the ultrasonic imaging apparatus 1 related to Embodiment 1, displays an image (C plane image) along a plane (C plane) almost parallel to a plane on which ultrasonic transducers are arranged on the display part 71. Then, when the operator designates a range for gain adjustment on the image via the input part 72, the ultrasonic imaging apparatus 1A adjusts brightness of the ultrasonic image by adjusting the intensity of the transmitting signals of ultrasonic waves. The ultrasonic imaging apparatus 1 related to Embodiment 1 changes the intensity of received signals. In contrast, the ultrasonic imaging apparatus 1A related to Embodiment 2 adjusts the brightness of the ultrasonic image by changing the intensity of transmitting signals. As a method of adjusting the intensity of transmitting signals, there are a method of changing size of the amplitude of the transmitting signals and a method of changing size of the transmitting aperture of the ultrasonic waves. First, the method of changing size of the amplitude of the transmitting signals is described, and next, the method of changing size of the transmitting aperture is described.

Amplitude Change of Transmitting Signals

The ultrasonic imaging apparatus 1A related to Embodiment 2 is provided with a transmitting signal intensity-adjusting part 31 and an aperture setting part 32 on the transmitting part 3, instead of the received signal intensity-adjusting part 41 and the received signal intensity-adjusting part 51 with which the ultrasonic imaging apparatus 1 related to Embodiment 1 is provided. The configuration other than those is the same as the configuration of the ultrasonic imaging apparatus 1 related to Embodiment 1, so the description is omitted. Hereinafter, the configuration of the ultrasonic imaging apparatus 1A is described, particularly focusing on the transmitting part 3.

First, the method of adjusting the intensity of the transmitting signals by changing the amplitude of the transmitting signals is described. Upon receipt of information indicating the positions of scanning lines and the gain from the control part 8, the transmitting signal intensity-adjusting part 31 increases the amplitude of the transmitting signals on the scanning lines in accordance with the gain. Consequently, the intensity of the transmitting signals becomes higher. As described, brightness of an ultrasonic image can be adjusted also by adjusting the intensity of transmitting signals, instead of gain adjustment for received signals.

Incidentally, a method of designating a range to be gain-adjusted, a method of determining a gain, and a method of specifying the positions of scanning lines are the same as those of the ultrasonic imaging apparatus 1 related to Embodiment 1 described above. In other words, a C plane image is displayed on the display part 71 and the operator designates an arbitrary range on the C plane image via the input part 72, thereby facilitating designation of a range for gain adjustment in a three-dimensional space. The image-processing part 6 specifies scanning lines passing through the range for gain adjustment and outputs information indicating the positions of the scanning lines to the control part 8. The control part 8 determines the gain, and outputs the information indicating the scanning lines and the gain to the transmitting signal intensity-adjusting part 31. The transmitting signal intensity-adjusting part 31 changes the amplitude of the transmitting signals on the scanning lines in accordance with the gain.

As described above, it becomes possible to easily designate a range for gain adjustment in a three-dimensional space by displaying a C plane image on the display part 71 and by designating the range for gain adjustment on the C plane image.

Operation

Figure 9:
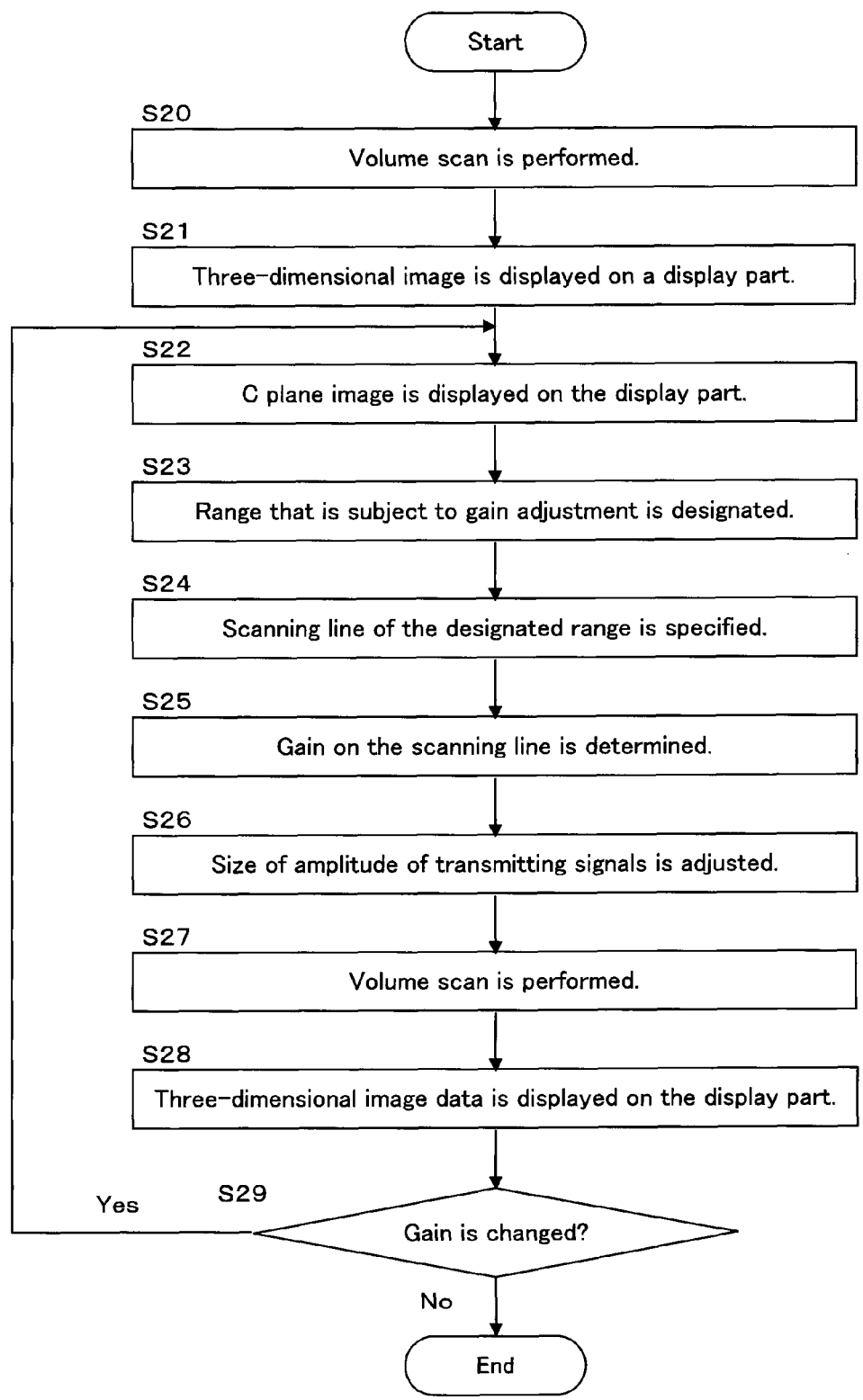
FIG. 9 is a flow chart sequentially showing operations of the ultrasonic imaging apparatus related to Embodiment 2 of the present invention.

The operation of the ultrasonic imaging apparatus 1A related to Embodiment 2 of the present invention is described with reference to FIG. 9. FIG. 9 is a flow chart sequentially showing operations of the ultrasonic imaging apparatus related to Embodiment 2 of the present invention.

Step S20

First, by applying the ultrasonic probe 2 to the body surface of a subject to be examined, a volume scan (3D scan) is performed using the ultrasonic probe 2.

Step S21

The image-processing part 6 generates a three-dimensional image data by applying volume rendering to the volume data obtained by the scan using the ultrasonic probe 2. A three-dimensional image based on this three-dimensional image data is displayed on the display part 71.

Step S22

Then, when the operator gives an instruction of gain adjustment via the input part 72, the image-processing part 6 generates image data of an arbitrary cross section by applying the MPR processing to volume data. For example, when the operator designates an arbitrary C plane via the input part 72, the image-processing part 6 generates image data along the C plane (C plane image data). A C plane image based on this C plane image data is displayed on the display part 71.

Step S23

In the state where the C plane image is displayed on the display part 71, the operator designates an arbitrary range on the C plane image via the input part 72. This designated range is set as a range for gain adjustment. When the range for gain adjustment is designated in this way, coordinate information of the range on the C plane image is output from the user interface 7 to the image-processing part 6.

Step S24

Upon receipt of the coordinate information of the range for gain adjustment from the input part 72, the image-processing part 6 specifies scanning lines passing through the range and outputs information indicating the positions of the scanning lines to the control part 8.

Step S25

Upon receipt of the coordinate information of the range for gain adjustment from the image-processing part 6, the control part 8 determines the gain in the range. The method of determining the gain is the same as the configuration of the ultrasonic imaging apparatus 1 related to Embodiment 1 described above, so the description is omitted. Then, the control part 8 outputs information indicating the positions of the scanning lines and the gain to the transmitting signal intensity-adjusting part 31 of the transmitting part 3.

Step S26

Upon receipt of information indicating the positions of the scanning lines and the gain from the control part 8, the transmitting signal intensity-adjusting part 31 of the transmitting part 3 adjusts the intensity of transmitting signals on the scanning lines in accordance with the gain. For example, the transmitting signal intensity-adjusting part 31 increases the size of amplitude of the transmitting signals in accordance with the gain. Consequently, the intensity of the transmitting signals becomes higher.

Step S27

Then, the ultrasonic probe 2 performs a volume scan using the gain-adjusted transmitting signal.

Step S28

The received signals obtained by the scan are output to the image-processing part 6 via the receiving part 4 and the signal-processing part 5. The image-processing part 6 generates image data such as three-dimensional image data by applying image processing such as volume rendering to the volume data. An image based on this image data is displayed on the display part 71. This image is an image obtained by the gain-adjusted transmitting signals, accordingly an image whose brightness is adjusted. For example, if the gain of a dark part is adjusted, the brightness of the dark part is high, so an image in which the brightness is wholly uniform is to be obtained.

Step S29

The operator observes this gain-adjusted image to determine whether the set gain is necessary to be changed or not (step S29). For example, when the brightness of the ROI is not appropriate, it is determined that there is a need to change the gain, and the operator gives an instruction of gain adjustment again (step S29, Yes). Consequently, processing from step S22 to step S28 are repeated. At this time, the operator instructs brightness adjustment by changing a range to be gain-adjusted or by changing a gain curve. On the other hand, when the operator determines that there is no need to change the gain, the transmitting signal intensity-adjusting part 31 performs gain adjustment afterward in accordance with the gain and the range of gain adjustment set by from step S22 to step S28.

As described above, it becomes possible to easily designate a range in a three-dimensional space by displaying a C plane image through which scanning lines pass and by designating the range for gain adjustment on the C plane image.

In addition, as is the case with the ultrasonic imaging apparatus 1 related to Embodiment 1, an image (tomographic image) along a plane perpendicular to the C plane (tomographic plane) may be displayed on the display part 71 at the time of displaying the C plane image. Consequently, capturing a position in a three-dimensional space is facilitated. Furthermore, an image other than the C plane image, the image of a plane intersecting the scanning lines may be created and a range for gain adjustment may also be designated on the image.

Change of Transmitting Aperture

Next, the method of adjusting the intensity of the transmitting signals by changing size of a transmitting aperture of the ultrasonic waves is described. Upon receipt of the information indicating the positions of the scanning lines and the gain from the control part 8, the aperture setting part 32 of the transmitting part 3 increases the aperture area of the ultrasonic waves of the part corresponding to the positions of the scanning lines in the ultrasonic transducers of the ultrasonic probe 2. The transmitting part 3 allows the ultrasonic probe 2 to transmit/receive the ultrasonic waves in accordance with size of the aperture set by the aperture setting part 32. Consequently, the intensity of the transmitting signals of the ultrasonic waves becomes higher, so it becomes possible to increase the brightness of the dark part. Incidentally, it becomes possible to allow the intensity of the transmitting signals higher than by normal scan by providing the aperture area larger than usual when scanning without using the whole aperture of ultrasonic waves in the normal scan to increase the brightness of the dark part.

Incidentally, the signal intensity-adjusting part 31, the aperture setting part 32, the image-processing part 6, and the control part 8 may be implemented by hardware, or may be implemented by software. For example, the signal intensity-adjusting part 31, the aperture setting part 32, the image-processing part 6, and the control part 8 are implemented by a CPU, respectively. Then, a transmitting signal intensity adjusting program for executing functions of the transmitting signal intensity-adjusting part 31, an aperture setting program for executing functions of the aperture setting part 32, an image processing program for executing functions of the image-processing part 6, and a program for executing functions of the control part 8 are pre-stored on a not shown storage part. Then, the CPU executes functions of the transmitting signal intensity-adjusting part 31 by executing the transmitting signal intensity adjusting program stored on the not shown storage part. In addition, the CPU executes functions of the aperture setting part 32 by executing the aperture setting program. In addition, the CPU executes functions of the image-processing part 6 by executing the image processing program. In addition, the CPU executes functions of the control part 8 by executing the program executing functions of the control part 8.

MODIFICATION EXAMPLES

Next, modification examples of the embodiments described above are described.

Modification Example 1

Figure 10A:
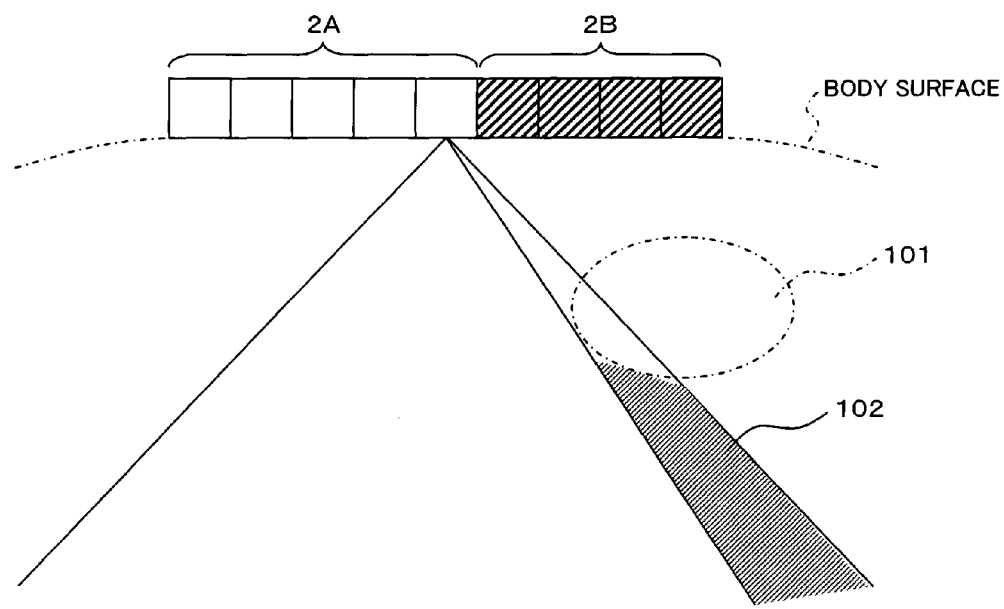
FIG. 10A is a view of an aperture of an ultrasonic probe and is a cross-sectional drawing of an ultrasonic transducer.
Figure 10B:
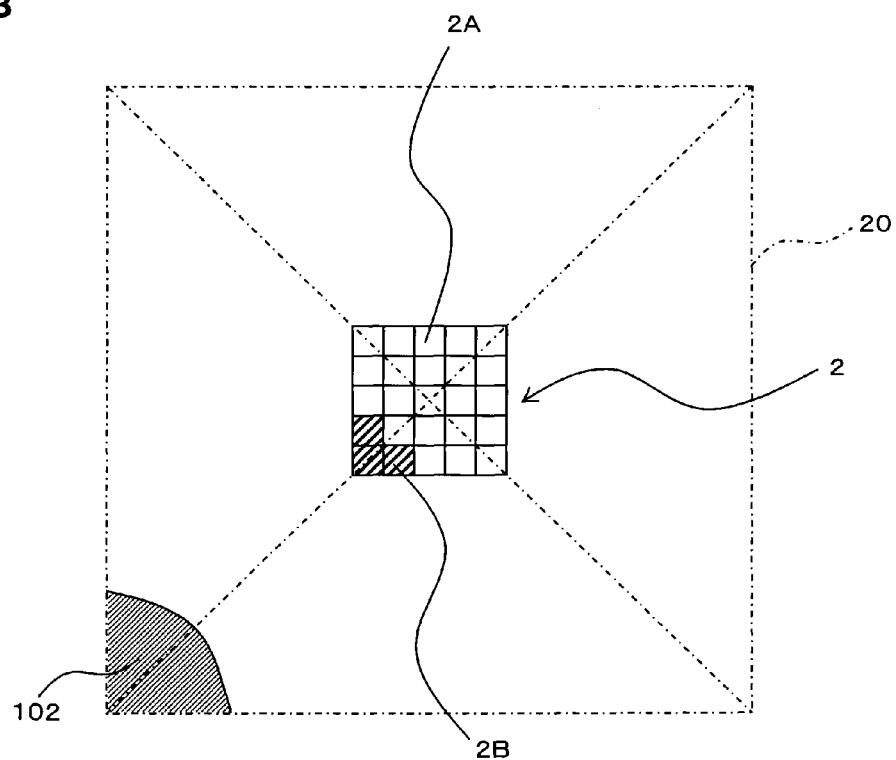
FIG. 10B is a view of an aperture of an ultrasonic probe and is a view from the ultrasonic probe (top view).

First, as a Modification Example 1, a modification example of the operation of the ultrasonic imaging apparatus 1A related to Embodiment 2 is described with reference to FIG. 10A and FIG. 10B. FIG. 10A is a view of an aperture of an ultrasonic probe and is a cross-sectional drawing of an ultrasonic transducer. FIG. 10B is a view of an aperture of an ultrasonic probe and is a view from the ultrasonic probe (top view).

As shown in FIG. 10A, as a factor of occurrence of the dark part 102 in the ROI, the presence of a highly reflective part (obstacle) 101 such as a rib is conceivable. If there exists the highly reflective part (obstacle) 101 such as the rib within the range to be scanned using ultrasonic waves, the ultrasonic waves are reflected by the highly reflective part 101, accordingly the parts behind the highly reflective part 101 becomes the dark part 102. In such a case, the brightness of the ultrasonic image can be increased by increasing the intensity of the transmitting signals of ultrasonic waves, however, reflection waves of the ultrasonic waves by the obstacle are inevitable.

Therefore, in Modification Example 1, when scanning the region of the dark part 102 using the ultrasonic probe 2, the region of the dark part 102 is scanned, without using ultrasonic transducers close to the region of the dark part 102, by using ultrasonic transducers in other part. On the other hand, when scanning regions other than the dark part 102, a scan is performed with all ultrasonic transducers. In other words, when scanning the of the dark part 102 is scanned, without using apertures close to the region of the dark part 102, by using apertures in other part, while when scanning regions other than the dark part 102, the regions is scanned with all apertures.

Upon receipt of the information indicating the positions of the scanning lines (information indicating of the position of the dark part 102) from the control part 8, the aperture setting part 32 set an aperture other than apertures close to the positions to the transmitting part 3. For example, upon receipt of the information indicating the positions of the scanning lines from the control part 8, the aperture setting part 32 defines a range including the positions of the scanning lines, the range with preset width, as apertures not to be used, and sets apertures other than those to the transmitting part 3. When scanning the dark part 102, the transmitting part 3 allows the ultrasonic probe 2 to transmit/receive ultrasonic waves in accordance with the aperture set by the aperture setting part 32. On the other hand, when scanning regions other than the dark part 102, the transmitting part 3 allows the ultrasonic probe 2 to transmit/receive ultrasonic waves by using all apertures.

For example, in the examples shown in FIG. 10A and FIG. 10B, when scanning the region of the dark part 102, the transmitting part 3 scans the region of the dark part 102, without using the group 2B of ultrasonic transducers close to the dark part 102, by using a group 2A of ultrasonic transducers in other part. Consequently, it allows to reduce the effect of the reflection of ultrasonic waves due to the obstacle. On the other hand, when scanning regions other than the dark part 102, the transmitting part 3 performs a scan by all ultrasonic transducers.

As described, the apertures become small when scanning the region of the dark part 102, so the intensity of the transmitting signals of ultrasonic waves decreases. Therefore, in order to compensate for the decrease, the transmitting signal intensity-adjusting part 31 increases the amplitude of the transmitting signals. In this case, the control part 8 outputs the information indicating the positions of the scanning lines to the aperture setting part 32 and outputs the gain for compensating for the decrease of the signal intensity to the transmitting signal intensity-adjusting part 31. The aperture setting part 32 sets apertures to be used or not to be used to the transmitting part 3 in accordance with the information indicating the positions of the scanning lines. The transmitting signal intensity-adjusting part 31 changes size of the amplitude of the transmitting signals in accordance with the gain.

As described above, scanning without employing ultrasonic transducers close to the designated range (dark parts) allows to reduce the effect of the reflection of ultrasonic waves by an obstacle. Moreover, uniformed brightness of the ultrasonic image is achieved by increasing the intensity of the transmitting signals of ultrasonic waves for compensating for the reduced aperture.

In addition, methods of Embodiment 1 and Embodiment 2 described above might be combined. For example, gain adjustment may be performed at the time of transmission and receipt by increasing the intensity of the transmitting signals and by increasing the intensity of the received signals.

Modification Example 2

Figure 11:
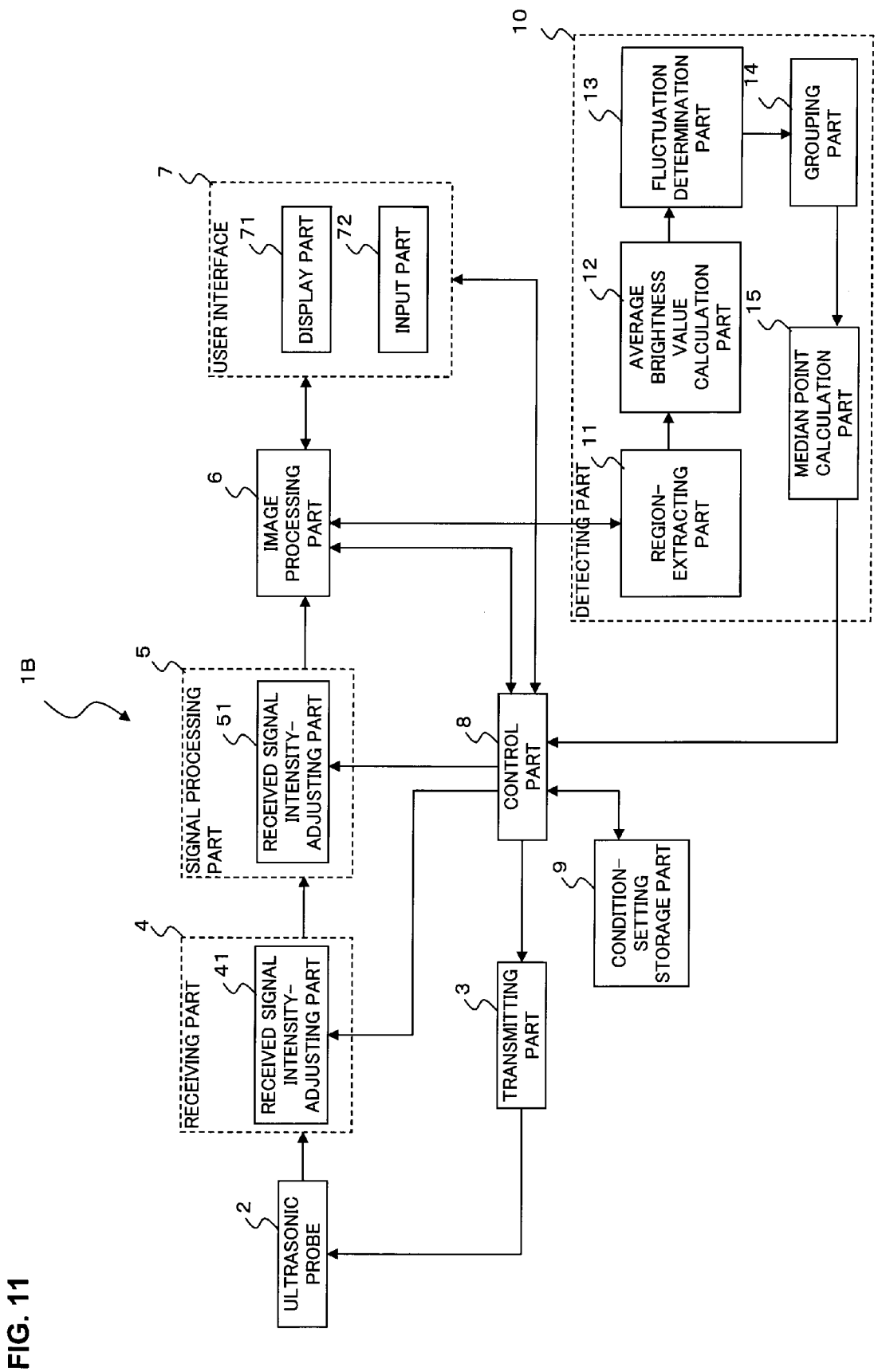
FIG. 11 is a block diagram showing the ultrasonic imaging apparatus related to Modification Example 2.
Figure 12:
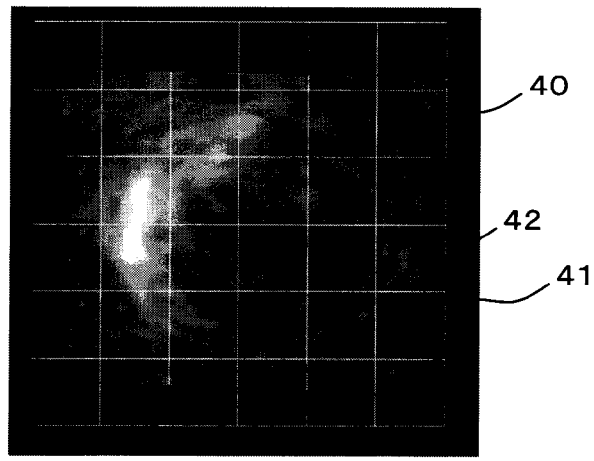
FIG. 12 is a view schematically showing a plurality of regions set on a C plane image.
Figure 13:
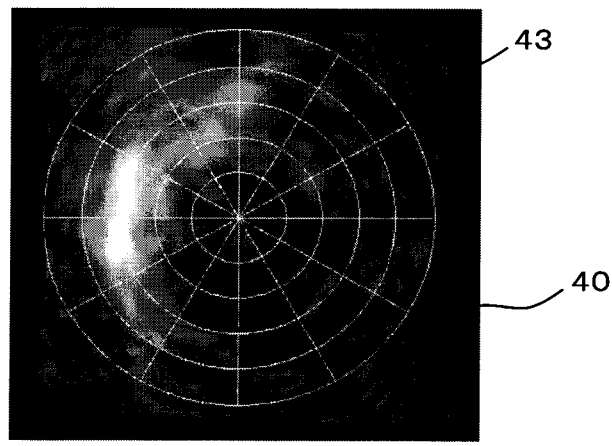
FIG. 13 is a view schematically showing a plurality of regions set on a C plane image.
Figure 14:
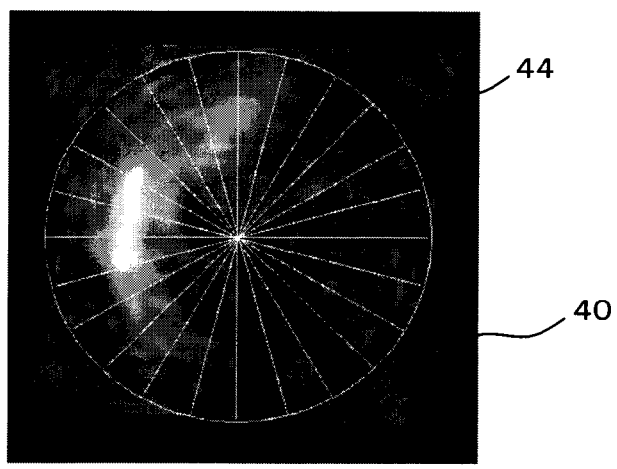
FIG. 14 is a view schematically showing a plurality of regions set on a C plane image.
Figure 15:
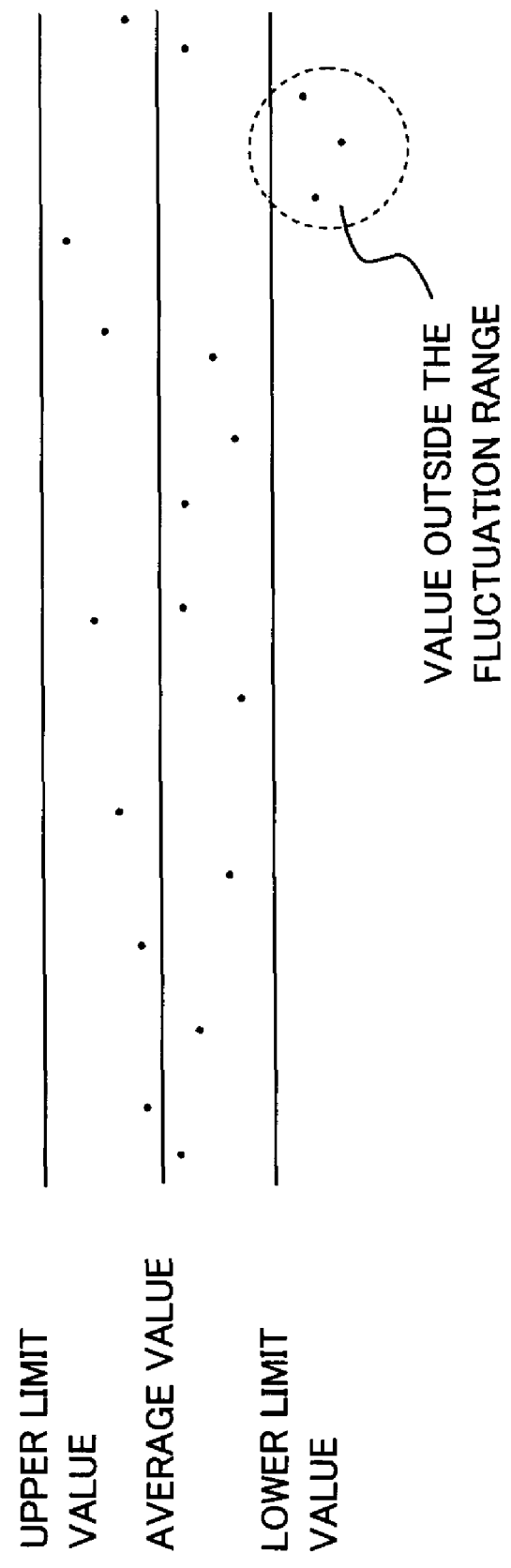
FIG. 15 shows the distribution of the brightness values.

Next, for Modification Example 2, an example of automatically detecting a range for gain adjustment is described with reference to FIG. 11 through FIG. 15. FIG. 11 is a block diagram showing the ultrasonic imaging apparatus related to Modification Example 2. FIG. 12 through FIG. 14 are views schematically showing a plurality of regions set on a C plane image. FIG. 15 shows the distribution of the brightness values. In the ultrasonic imaging apparatus 1B shown in FIG. 11, that indicating the same symbol as the ultrasonic imaging apparatus 1 related to Embodiment 1 has the same function, so the description is omitted. In Modification Example 2, the ultrasonic imaging apparatus 1 related to Embodiment 1 is further provided with a detecting part 10 for automatically detecting a range for gain adjustment. Hereinafter, the configuration of the detecting part 10 is described.

The detecting part 10 is configured to comprise a region-extracting part 11, an average brightness value calculation part 12, a fluctuation determination part 13, a grouping part 14, and a median point calculation part 15. The detecting part 10 divides the C plane image into a preset plurality of regions, determines the average value of the brightness values of pixels included in each region, and specifies a region in which the average value is outside a preset fluctuation range. Moreover, the detecting part 10 groups regions that are adjacent to the specified region into one group and determines the position of the median brightness point based on the distribution of brightness in regions belonging to the group. Then, the control part 8 determines the gain corresponding to the signals on each scanning line passing through a predetermined range centered on the position of the median point.

Upon receipt of the C plane image output from the image-processing part 6, the region-extracting part 11 extracts a region having the brightness value that is a predetermined threshold or above in the C plane image. This threshold is a value set for detecting a tissue of a subject to be examined, so the region in which the brightness value of the image is the threshold or above represents tissues of the subject to be examined. For example, the region-extracting part 11 extracts a region in which the brightness value is the threshold or above by detecting the boundary of a region in which the brightness value is less than the threshold.

The detecting processing of the boundary by the region-extracting part 11 is described with reference to FIG. 12. As shown in FIG. 12 for example, the region-extracting part 11 extracts a boundary 41 of the C plane image 40 and extracts a region included inside the boundary 41. The brightness value is less than the threshold outside the boundary 41, and the brightness value is the threshold or above inside the boundary 41. In the example shown in FIG. 12, the image inside the boundary 41 shows tissues of the subject to be examined.

The average brightness value calculation part 12 receives the coordinate information of each pixel and the brightness values of each pixel that are included in the region extracted by the region-extracting part 11, further divides the C plane image into a plurality of regions, and determines the average value of the brightness values of pixels included in each region. The control part 8 performs a setting for dividing the C plane image into a plurality of regions. Patterns of division are preset in the control part 8. The average brightness value calculation part 12 receives the information indicating a division pattern from the control part 8, divides the C plane image into a plurality of regions in accordance with the division pattern, and determines the average value of the brightness values of pixels included in each region. Then, the average brightness value calculation part 12 outputs the average value of the brightness values in each region to the fluctuation determination part 13.

Incidentally, a plurality of division patterns is preset in the control part 8, so the operator can select an arbitrary division pattern from the plurality of division patterns. For example, the control part 8 instructs the display part 71 to display the preset plurality of division patterns. Then, when the operator uses the input part 72 to designate an arbitrary division pattern among the plurality of division patterns, the control part 8 outputs the information indicating the designated division pattern to the average brightness value calculation part 12. The average brightness value calculation part 12 divides the C plane image into a plurality of regions in accordance with the division pattern and determines the average value of the brightness values of pixels included in each region.

Herein, the plurality of regions set on the C plane image is described with reference to FIG. 12 through FIG. 14.

For example, the division pattern 42 shown in FIG. 12 has a lattice-shaped pattern. Each region that is divided by the lattice-shaped pattern 42 has the same shape and the same size. The average brightness value calculation part 12 receives the coordinate information of each pixel and the brightness value of each pixel that are included in the region extracted by the region-extracting part 11, further receives the information indicating the division pattern 42 from the control part 8, and determines the average value of the brightness values of pixels included in each region.

Incidentally, the control part 8 may instruct the display part 71 to display the C plane image 40 generated by the image-processing part 6 and further instruct the display part 71 to display the division pattern 42 by overlapping on the C plane image 40.

Examples of division patterns are shown in FIG. 13 and FIG. 14. For example, the division pattern 43 shown in FIG. 13 has a concentric pattern and a line radiating from the center of the circle. In addition, the division pattern 44 shown in FIG. 14 has a circular pattern and a line radiating from the center of the circle. The division patterns 43 and 44 are set in the control part 8. When the operator designates the division pattern 43 or the division pattern 44, the control part 8 outputs the information indicating the designated division pattern 43 (44) to the average brightness value calculation part 12. The average brightness value calculation part 12 divides the C plane image into a plurality of regions in accordance with the division pattern 43 (44) and determines the average value of the brightness values included in each region.

Upon receipt of the average value of bright values in each region determined by the average brightness value calculation part 12, the fluctuation determination part 13 determines whether each average value is included within the fluctuation range. This fluctuation range is preset in the fluctuation determination part 13. For example, upon receipt of the average value of the brightness values in each region, the fluctuation determination part 13 further calculates the average of the average values and defines the calculated average value as the reference value of fluctuation. The fluctuation determination part 13 determines whether the average value of the brightness values in each region is included within the predetermined fluctuation range on the basis of the reference value. Then, the fluctuation determination part 13 specifies a region in which the average value of the brightness values is outside the fluctuation range. The fluctuation determination part 13 outputs the coordinate information of the region in which the average value of the brightness values is outside the fluctuation range to the grouping part 14.

This fluctuation range is shown in FIG. 15. In FIG. 15, the average value is the reference value determined by the fluctuation determination part 13 and is the basis for fluctuation determination. The upper limit value (maximum threshold) and the lower limit value (minimum threshold) are values for defining the fluctuation range on the basis of the reference value. The upper limit value (maximum threshold) and the lower limit value (minimum threshold) are preset in the fluctuation determination part 13. When the average value of the brightness values in each region is included between the upper limit value and the lower limit value, the fluctuation determination part 13 determines that the average value of the brightness values of the region is within the fluctuation range. On the other hand, when the average value of the brightness values in each region is a value exceeding the upper limit value or the lower limit value, the fluctuation determination part 13 determines that the average value of the brightness values in the region is outside the fluctuation range. As shown in FIG. 15 for example, the fluctuation determination part 13 determines the average that is less than the lower limit value (minimum threshold) as is outside of the fluctuation range. Then, the fluctuation determination part 13 outputs the coordinate information of the region in which the average value of the brightness values is outside of the fluctuation range to the grouping part 14.

The grouping part 14 associates regions that are adjacent to the regions in which the average value is determined to be outside the fluctuation range with each other as one group.

The median point calculation part 15 determines the median brightness point, based on the distribution of brightness in each region associated with each other as one group by the grouping part 14. For example, the median point calculation part 15 determines the position of the median brightness point of the regions belonging to the group, based on the brightness value of each pixel and the position of each pixel included in each region associated with each other as one group by the grouping part 14, and the area occupied by the regions belonging to the group. Then, the median point calculation part 15 outputs the coordinate information of the position of the median brightness point to the control part 8.

Upon receipt of the coordinate information of the median point position from the median point calculation part 15, the control part 8 determines the gain for the signals on each scanning line passing through the predetermined range that is preset centered on the position of the median point. For example, the control part 8 determines the gain for the signals on each scanning line passing through the predetermined range centered on the position of the median point in accordance with the preset gain curve as shown in FIG. 5.

Then, as is the case with Embodiment 1, the control part 8 outputs the information indicating the positions of the scanning lines and the gain to the received signal intensity-adjusting part 41 of the receiving part 4. Upon the receipt of the information indicating the positions of the scanning lines and the gain from the control part 8, the received signal intensity-adjusting part 41 of the receiving part 4 changes the intensity of the signals on the scanning lines among signals output from the ultrasonic probe 2 in accordance with the gain. In addition, the control part 8 may output the information indicating the positions of the scanning lines and the gain to the received signal intensity-adjusting part 51 of the signal-processing part 5 instead of the received signal intensity-adjusting part 41 of the receiving part 4. Upon receipt of the information indicating the positions of the scanning lines and the gain from the control part 8, the received signal intensity-adjusting part 51 changes the intensity of the signals after being converted into digital signals, the signals being on the scanning lines, in accordance with the gain. In addition, as is the case with Embodiment 2, the control part 8 may output the information indicating the positions of the scanning lines and the gain into the transmitting signal intensity-adjusting part 31 shown in FIG. 8 instead of the received signal intensity-adjusting part 41 or the received signal intensity-adjusting part 51. Upon receipt of the information indicating the positions of the scanning lines and the gain from the control part 8, the transmitting signal intensity-adjusting part 31 increases the amplitude of the transmitting signals on the scanning lines in accordance with the gain. Consequently, the intensity of the transmitting signals becomes higher.

As described above, also in Modification Example 2, any adjustment of the analog gain adjustment, the digital gain adjustment, or the transmitting signal adjustment is performed.

In addition, when each region is divided into a plurality groups by the grouping part 14, the median point calculation part 15 determines the position of the median brightness point for each group and outputs the coordinate information of the position of the median point of each group to the control part 8. Upon the receipt of the coordinate information of the plurality of the positions of the median points, the control part 8 adjusts the gain for the signals on the scanning lines passing through the predetermined range centered on each position of the median point in accordance with the preset gain.

According to the ultrasonic imaging apparatus 1B having the above configuration, even when there is a decrease of the brightness due to a local shadow, it becomes possible to automatically detect the shadow part and automatically adjust the whole brightness.

In addition, the ultrasonic imaging apparatus 1B related to Modification Example 2 may determine a range for the gain adjustment, based on the values of the signals on the scanning lines passing through the C plane.

In addition, the detecting part 10 may be implemented by hardware, or may be implemented by software. For example, the detecting part 10 is implemented by a CPU, and a detecting program for executing functions of the detecting part 10 are pre-stored on a not shown storage part. This detecting program is configured to comprise a region extracting program for executing functions of the region-extracting part 11, an average brightness value calculating program for executing functions of the average brightness value calculation part 12, a fluctuation determining program for executing functions of the fluctuation determination part 13, a grouping program for executing functions of the grouping part 14, and a position of the median point calculating program for executing functions of the median point calculation part 15. Then, the CPU executes functions of the detecting part 10 by executing the detecting program stored on the not shown storage part. In other words, the CPU respectively executes functions of the region-extracting part 11, functions of the average brightness value calculation part 12, functions of the fluctuation determination part 13, functions of the grouping part 14, and functions of the median point calculation part 15 by executing each program included in the detecting program.

Modification Example 3

Next, the ultrasonic imaging apparatus related to Modification Example 3 is described. This ultrasonic imaging apparatus related to Modification Example 3 has the same configuration as the ultrasonic imaging apparatus related to Modification Example 2 described above, and determines the gain for the signals on each scanning line passing through a predetermined range centered on the position of the median point. Furthermore, the ultrasonic imaging apparatus related to Modification Example 3 determines the position of the median point for a plurality of C planes with difference depth, determines the gain for the signals on the scanning lines passing through the predetermined range centered on the position of the median point in each depth, and performs the weighting processing for the determined gain to determine the gain for the signals on each scanning line.

First, when the operator designates a plurality of depths via the input part 72, the image-processing part 6 generates a plurality of C plane image data with different depth in accordance with the designation. Then, the image-processing part 6 outputs the plurality of C plane image data to the detecting part 10.

The detecting part 10 determines the position of the median point of the range for brightness adjustment for each C plane image in each depth by applying the same processing as in the case of Modification Example 2 to the plurality C plane image data generated by the image-processing part 6. Then, the detecting part 10 outputs the coordinate information of the position of the median point determined for each C plane image in each depth to the control part 8.

Upon receipt the position of the median point determined for each C plane image in each depth from the median point calculation part 15, the control part 8 determines the gain for the signals on each scanning line passing through a predetermined range centered on the position of the median point for each depth. For example, the control part 8 determines the gain for the signals on each scanning line passing through the predetermined range centered on the position of the median point for each depth in accordance with the preset gain curve as shown in FIG. 6. In other words, the control part 8 determines the gain for the signals on each scanning line passing through the predetermined range centered on the position of the median point of each depth.

Moreover, the control part 8 determines the gain for the signals on each scanning line in accordance with the weighing set for the C plane in each depth. The operator can use the input part 72 to designate the weighting for the C plane in each depth. Specifically, the control part 8 performs weighting for the C plane in each depth to the gain for the signals on each scanning line passing through the predetermined range centered on the position of the median point of each depth and determines the average value of the weighted gains.

Then, the control part 8 defines the average value of the gains as the gain for the signals on the whole scanning lines and outputs the information indicating the positions of the scanning lines and the average value of the gains to the received signal intensity-adjusting part 41, the received signal intensity-adjusting part 51, or the transmitting signal intensity-adjusting part 31. The received signal intensity-adjusting part 41, the received signal intensity-adjusting part 51, or the transmitting signal intensity-adjusting part 31 adjusts the gain, as is the cases with Embodiment 1 and Embodiment 2, by employing the average value of the gains output from the control part 8.

For example, when the weight set for the C planes at the third, fourth, and fifth deepest position depthwise is "1" and the weight set for the C planes at the other depth is "0," the control part 8 performs weighting of each depth to the gain for the signals on each scanning line passing through a predetermined range centered on the position of the median point of each depth. Moreover, the control part 8 determines the average value of the weighted gains in each depth. Since the weight set for the C planes at the third, fourth, and fifth deepest position depthwise is "1" in this example, the control part 8 determines the average value of the gains for the signals on each scanning line passing through a predetermined range centered on the third, fourth, and fifth deepest position of the median point. More particularly, the control part 8 determines the average value of the following gains: the gain for the signals on each scanning line passing through a predetermined range centered on the third deepest position of the median point; the gain for the signals on each scanning line passing through a predetermined range centered on the fourth deepest position of the median point; and the gain for the signals on each scanning line passing through a predetermined range centered on the fifth deepest position of the median point. Then, the control part 8 defines the average value of the gains as the gain for the signals on the whole scanning lines, and outputs the information indicating the positions of the scanning lines and the average value of the gains to the received signal intensity-adjusting part 41, the received signal intensity-adjusting part 51, or the transmitting signal intensity-adjusting part 31.

In addition, provided that the weight set for the C planes at the first, second, third, fourth, fifth, and sixth deepest position depthwise is respectively "0.0," "0.1," "0.3," "0.7," "0.8," and "0.3," the control part 8 performs weighting of each depth to the gain for the signals on each scanning line passing through a predetermined range centered on the position of the median point of each depth. Moreover, the control part 8 determines the average value of the weighted gains in each depth. More particularly, the control part 8 performs the weighting of "0.0" to the gain for the signals on each scanning line passing through a predetermined range centered on the first deepest position of the median point, performs the weighting of "0.1" to the gain for the signals on each scanning line passing through a predetermined range centered on the second deepest position of the median point, performs the weighting of "0.3" to the gain for the signals on each scanning line passing through a predetermined range centered on the third deepest position of the median point, performs the weighting of "0.7" to the gain for the signals on each scanning line passing through a predetermined range centered on the fourth deepest position of the median point, performs the weighting of "0.8" to the gain for the signals on each scanning line passing through a predetermined range centered on the fifth deepest position of the median point, and further performs the weighting of "0.3" to the gain for the signals on each scanning line passing through a predetermined range centered on the sixth deepest position of the median point. Then, the control part 8 determines the average value of the weighted gains. Then, the control part 8 defines the average value of the gains as the gain for the signals on the whole scanning lines, and outputs the information indicating the positions of the scanning lines and the average value of the gains to the received signal intensity-adjusting part 41, the received signal intensity-adjusting part 51, or the transmitting signal intensity-adjusting part 31.

As described above, a position of the median point is determined for a plurality of C planes with different depth, the gain for the signals on each scanning line passing through a predetermined range centered on the position of the median point in each depth is determined, and the weighting processing is performed to the determined gain to determine the gain for the signals on each scanning line. As a result, gain can be adjusted more locally.

What is claimed is:

1. An ultrasonic imaging apparatus comprising:
   an ultrasonic probe configured to three-dimensionally transmit and receive ultrasonic waves on scanning lines with an arrangement of ultrasonic transducers,
   an image-processing part configured to generate three-dimensional volume data based on a first set of signals derived from a first set of ultrasonic waves transmitted and received by the ultrasonic probe,
   a display part configured to display a first ultrasonic image representing a plane intersecting the scanning lines and being based on the first set of signals, and
   a signal intensity-adjusting part configured to change a gain of a second set of signals that correspond to scanning lines, among the scanning lines on which the ultrasonic waves are transmitted and received, that pass through a range of the plane corresponding to a brightness adjustment range by changing a size of an amplitude, at a time of transmission, of a second set of ultrasonic waves transmitted by the ultrasonic probe, wherein
   the brightness adjustment range is a range of the first ultrasonic image designated for brightness adjustment corresponding to the range of the plane, and
   the image-processing part is configured to generate a second ultrasonic image by correcting the three-dimensional volume data generated by the image-processing part based on the gain changed by the signal intensity-adjusting part and projecting the corrected three-dimensional volume data on a two-dimensional surface, and the display part displays the second ultrasonic image.

2. An ultrasonic imaging apparatus according to claim 1, further comprising:
   a designating part configured to designate the brightness adjustment range on the first ultrasonic image displayed on the display part,
   wherein the signal intensity-adjusting part is configured to change the gain of the second set of signals that correspond to the scanning lines passing through the range of the plane corresponding to the designated brightness adjustment range.

3. An ultrasonic imaging apparatus according to claim 2, wherein
   a direction from the center of said first ultrasonic image is designated by the designating part, and
   the signal intensity-adjusting part is configured to change the gain of the second set of signals that correspond to the scanning lines passing through a range from a peripheral part to a center side of the plane, as the range of the plane, along the designated direction.

4. An ultrasonic imaging apparatus according to claim 1, further comprising:
   a detecting part configured to divide the first ultrasonic image into a preset plurality of regions, to determine an average value of brightness values of pixels included in each region, and to specify a region in which the average value is outside a preset fluctuation range,
   wherein the signal intensity-adjusting part is configured to change the gain of the second set of signals that correspond to the scanning lines passing through the plane and correspond to regions including the specified region.

5. An ultrasonic imaging apparatus according to claim 4, wherein
the detecting part is configured to group regions that are adjacent to the specified region into one group and determine a position of a median point of brightness, based on the brightness values of pixels included in the one group, based on a distribution of brightness in regions belonging to the group, and
the signal intensity-adjusting part is configured to change the gain of the second set of signals that correspond to the scanning lines passing through a predetermined range centered on a position of the plane, as the range of the plane, that corresponds to the median brightness point.

6. An ultrasonic imaging apparatus according to claim 1, wherein
the image-processing part is configured to generate, as the first ultrasonic image, an image representing a plane that is substantially parallel to a plane on which the ultrasonic transducers are arranged.

7. An ultrasonic imaging apparatus according to claim 1, wherein
the image-processing part is configured to generate the first ultrasonic image, based on the first set of signals derived from the first set of ultrasonic waves transmitted and received by the ultrasonic probe, and to generate a third ultrasonic image along a plane including at least one of the scanning lines, and
the display part is configured to display the first ultrasonic image and the third ultrasonic image.

8. An ultrasonic imaging apparatus according to claim 1, wherein
the signal intensity-adjusting part is configured to gradually change the gain of the second set of signals that correspond to the scanning lines that pass through the range of the plane corresponding to the brightness adjustment range.

9. An ultrasonic imaging apparatus according to claim 1, wherein
the signal intensity-adjusting part is configured to change the gain of the second set of signals that correspond to the scanning lines that pass through the range of the plane corresponding to the brightness adjustment range before the first set of signals derived from the first set of ultrasonic waves transmitted and received by the ultrasonic probe are converted into digital signals.

10. An ultrasonic imaging apparatus according to claim 1, wherein
the signal intensity-adjusting part is configured to change the gain of the second set of signals that correspond to the scanning lines that pass through the range of the plane corresponding to the brightness adjustment range after the first set of signals derived from the first set of ultrasonic waves transmitted and received by the ultrasonic probe are converted into digital signals.

11. An ultrasonic imaging apparatus according to claim 1, wherein
the signal intensity-adjusting part is configured to change the gain of the second set of signals that correspond to the scanning lines that pass through the range of the plane corresponding to the brightness adjustment range, before and after the first set of signals derived from the first set of ultrasonic waves transmitted and received by the ultrasonic probe are converted into digital signals.

12. An ultrasonic imaging apparatus according to claim 1, wherein
the signal intensity-adjusting part is configured to change the gain of the second set of signals that correspond to the scanning lines that pass through the range of the plane corresponding to the brightness adjustment range by changing a gain of a subset of the second set of signals that correspond to the scanning lines that pass through the range of the plane corresponding to the brightness adjustment range among the second set of signals derived from the second set of ultrasonic waves transmitted and received by the ultrasonic probe.

13. An ultrasonic imaging apparatus according to claim 1, wherein
the signal intensity-adjusting part is configured to change the gain of the second set of signals that correspond to the scanning lines that pass through the range of the plane corresponding to the brightness adjustment range at the time of the transmission by changing a size of a transmitting aperture of the second set of ultrasonic waves transmitted by the ultrasonic probe.

14. A method of obtaining an ultrasonic image comprising:
transmitting and receiving ultrasonic waves on scanning lines, by an ultrasonic probe on which ultrasonic transducers are arranged, three-dimensionally,
generating three-dimensional volume data based on a first set of signals derived from a first transmitting and receiving of ultrasonic waves,
changing a gain of a second set of signals that correspond to scanning lines, among the scanning lines on which the ultrasonic waves are transmitted and received, that pass through a range of a plane corresponding to a brightness adjustment range, the plane intersecting the scanning lines of ultrasonic waves, by changing a size of an amplitude, at a time of transmission, of a second transmitting of ultrasonic waves by the ultrasonic probe, wherein the brightness adjustment range is a range of a first ultrasonic image designated for brightness adjustment corresponding to the range of the plane,
generating a second ultrasonic image based on the second set of signals by correcting the three-dimensional volume data and projecting the corrected three-dimensional volume data on a two-dimensional surface, and
displaying the second ultrasonic image.

15. A method of obtaining an ultrasonic image according to claim 14, further comprising:
displaying the first ultrasonic image after generating the first ultrasonic image, and
receiving a designation of the brightness adjustment range designated on the first ultrasonic image displayed, wherein
at the step of changing, the gain of the second set of signals corresponding to the scanning lines passing through the range of the plane corresponding to the received brightness adjustment range is changed.

16. A method of obtaining an ultrasonic image according to claim 15, wherein
at the step of receiving, an input of a direction from a center of the first ultrasonic image displayed is received, and
at the step of changing, the gain of the second set of signals corresponding to the scanning lines passing through a range from a peripheral part to a center side of the plane, as the range of the plane, along the direction is changed.

17. A method of obtaining an ultrasonic image according to claim 14, further comprising:
dividing the first ultrasonic image into a preset plurality of ranges, determining an average value of brightness values of pixels included in each range, and specifying a range in which the average value is outside a preset fluctuation range, wherein at the step of changing, the gain of the second set of signals corresponding to the scanning lines passing through ranges including the specified range, as the range of the plane, is changed.

18. A method of obtaining an ultrasonic image according to claim 17, wherein at the step of dividing, ranges adjacent to the specified range are grouped into one group, and a position of a median point of brightness based on brightness values of pixels included in the one group is determined, based on a distribution of brightness in ranges belonging to the group, and at the step of changing, the gain of the second set of signals corresponding to the scanning lines passing through a predetermined range centered on a position of the plane, as the range of the plane, that corresponds to the median brightness point is changed.

19. A method of obtaining an ultrasonic image according to claim 14, wherein at the step of generating the three-dimensional volume data, as the first ultrasonic image, an image representing a plane that is substantially parallel to a plane on which the ultrasonic transducers are arranged is generated.

20. A method of obtaining an ultrasonic image according to claim 14, wherein at the step of generating the three-dimensional volume data, the first ultrasonic image is generated, based on the first set of signals derived from the first transmitting and receiving of the ultrasonic waves, and a third ultrasonic image along a plane including at least one of the scanning lines is generated, and then, the first ultrasonic image and the third ultrasonic image are displayed.

21. A method of obtaining an ultrasonic image according to claim 14, wherein at the step of changing, the gain of the second set of signals corresponding to the scanning lines that pass through the range of the plane corresponding to the brightness adjustment range is gradually changed.

22. A method of obtaining an ultrasonic image according to claim 14, wherein at the step of changing, the gain of the second set of signals corresponding to the scanning lines that pass through the range of the plane corresponding to the brightness adjustment range is changed before the first set of signals derived from the first transmitting and receiving of the ultrasonic waves are converted into digital signals.

23. A method of obtaining an ultrasonic image according to claim 14, wherein at the step of changing, the gain of the second set of signals corresponding to the scanning lines that pass through the range of the plane corresponding to the brightness adjustment range is changed after the first set of signals derived from the first transmitting and receiving of the ultrasonic waves are converted into digital signals.

24. A method of obtaining an ultrasonic image according to claim 14, wherein at the step of changing, the gain of the second set of signals corresponding to the scanning lines that pass through the range of the plane corresponding to the brightness adjustment range is changed, before and after the first set of signals derived from the first transmitting and receiving of the ultrasonic waves are converted into digital signals.

25. A method of obtaining an ultrasonic image according to claim 14, at the step of changing, the gain of the second set of signals corresponding to the scanning lines that pass through the range of the plane corresponding to the brightness adjustment range is changed by changing a gain of a subset of the second set of signals that correspond to the scanning lines that pass through the range of the plane corresponding to the brightness adjustment range among the second set of signals the second transmitting and receiving of the ultrasonic waves by the ultrasonic probe.

26. A method of obtaining an ultrasonic image according to claim 14, wherein at the step of changing, the gain of the second set of signals corresponding to the scanning lines that pass through the range of the plane corresponding to the brightness adjustment range at the time of the transmission is changed by changing a size of a transmitting aperture for the second transmitting of ultrasonic waves by the ultrasonic probe.

* * * * *